(12) United States Patent
Stigall et al.

(10) Patent No.: US 10,687,832 B2
(45) Date of Patent: Jun. 23, 2020

(54) METHODS AND DEVICES FOR THROMBUS DISPERSAL

(71) Applicants: Jeremy Stigall, Carlsbad, CA (US); Joe Lauinger, San Diego, CA (US)

(72) Inventors: Jeremy Stigall, Carlsbad, CA (US); Joe Lauinger, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 122 days.

(21) Appl. No.: 15/037,011

(22) PCT Filed: Nov. 18, 2014

(86) PCT No.: PCT/US2014/066112
§ 371 (c)(1),
(2) Date: May 16, 2016

(87) PCT Pub. No.: WO2015/074036
PCT Pub. Date: May 21, 2015

(65) Prior Publication Data
US 2016/0262777 A1 Sep. 15, 2016

Related U.S. Application Data

(60) Provisional application No. 61/905,426, filed on Nov. 18, 2013.

(51) Int. Cl.
*A61B 17/22* (2006.01)
*A61B 18/24* (2006.01)
(Continued)

(52) U.S. Cl.
CPC ...... *A61B 17/2202* (2013.01); *A61B 17/3203* (2013.01); *A61B 18/1492* (2013.01);
(Continued)

(58) Field of Classification Search
CPC ............ A61B 17/2202; A61B 17/3203; A61B 18/1492; A61B 18/245
(Continued)

(56) References Cited

U.S. PATENT DOCUMENTS

| 4,794,931 A | 1/1989 | Yock |
| 4,807,620 A | 2/1989 | Strul et al. |

(Continued)

FOREIGN PATENT DOCUMENTS

WO 2013119662 A1 8/2013

OTHER PUBLICATIONS

Bail, M. et al "Optical Coherence Tomography with the "Spectral Radar" Fast Optical Analysis in Volume Scatterers by short Coherence Interferometry", Optics Letters, vol. 21, No. 14, 1996, pp. 1087-1089.

*Primary Examiner* — Phillip A Gray

(57) ABSTRACT

Catheter systems of the invention are directed to the removal of occlusions, such as thrombi and plaque, within blood vessels. In certain aspects, catheter systems of the invention include an elongate body defining a first lumen and comprising a distal portion, an inner member configured for insertion into the first lumen, the inner member comprising an energy source configured to deliver therapeutic energy to a treatment site; and a dissolution element coupled to the distal portion of the elongate body. The dissolution element may include a heating element, steam, and a balloon.

17 Claims, 25 Drawing Sheets

(51) Int. Cl.
  *A61B 17/3203* (2006.01)
  *A61B 18/14* (2006.01)
  *A61N 7/00* (2006.01)
  *A61M 25/10* (2013.01)
  *A61M 37/00* (2006.01)
  *A61B 18/00* (2006.01)
  *A61B 18/22* (2006.01)
  *A61B 17/00* (2006.01)
  *A61B 18/18* (2006.01)
  *A61B 90/00* (2016.01)

(52) U.S. Cl.
  CPC ......... *A61B 18/245* (2013.01); *A61M 25/104* (2013.01); *A61M 37/0092* (2013.01); *A61N 7/00* (2013.01); *A61B 2017/00084* (2013.01); *A61B 2017/00115* (2013.01); *A61B 2017/22021* (2013.01); *A61B 2017/22051* (2013.01); *A61B 2017/22061* (2013.01); *A61B 2017/22084* (2013.01); *A61B 2017/32035* (2013.01); *A61B 2018/00011* (2013.01); *A61B 2018/0022* (2013.01); *A61B 2018/00029* (2013.01); *A61B 2018/0041* (2013.01); *A61B 2018/00386* (2013.01); *A61B 2018/00577* (2013.01); *A61B 2018/00666* (2013.01); *A61B 2018/00791* (2013.01); *A61B 2018/00797* (2013.01); *A61B 2018/00809* (2013.01); *A61B 2018/00815* (2013.01); *A61B 2018/00821* (2013.01); *A61B 2018/00863* (2013.01); *A61B 2018/00904* (2013.01); *A61B 2018/00982* (2013.01); *A61B 2018/1467* (2013.01); *A61B 2018/1861* (2013.01); *A61B 2018/2211* (2013.01); *A61B 2018/2238* (2013.01); *A61B 2090/3784* (2016.02); *A61N 2007/0043* (2013.01); *A61N 2007/0078* (2013.01)

(58) Field of Classification Search
  USPC .......................................................... 604/22
  See application file for complete search history.

(56) References Cited

U.S. PATENT DOCUMENTS

| | | | |
|---|---|---|---|
| 4,834,093 A | 5/1989 | Littleford | |
| 4,841,977 A | 6/1989 | Griffith | |
| 4,909,258 A | 3/1990 | Kuntz et al. | |
| 4,917,097 A | 4/1990 | Eberle | |
| 4,951,677 A | 8/1990 | Abele | |
| 4,993,412 A | 2/1991 | Murphy-Chutorian | |
| 5,000,185 A | 3/1991 | Yock | |
| 5,032,123 A | 7/1991 | Katz | |
| 5,035,694 A | 7/1991 | Kasprzyk et al. | |
| 5,040,548 A | 8/1991 | Yock | |
| 5,041,108 A | 8/1991 | Coster | |
| 5,095,911 A | 3/1992 | Pomeranz | |
| 5,114,423 A * | 5/1992 | Kasprzyk ............... | A61B 18/08 604/913 |
| 5,125,137 A | 6/1992 | Christiaan | |
| 5,135,486 A | 8/1992 | Cortez | |
| 5,167,233 A | 12/1992 | Eberle | |
| 5,176,141 A | 1/1993 | Bom | |
| 5,176,674 A | 1/1993 | Hofmann | |
| 5,183,048 A | 2/1993 | Eberle | |
| 5,188,632 A | 2/1993 | Goldenberg | |
| 5,240,003 A | 8/1993 | Bom | |
| 5,243,988 A | 9/1993 | Sieben | |
| 5,313,949 A | 5/1994 | Yock | |
| 5,321,501 A | 6/1994 | Fujimoto | |
| 5,353,798 A | 10/1994 | Sieben | |
| 5,368,037 A | 11/1994 | Eberle | |
| 5,373,845 A | 12/1994 | Gardineer | |
| 5,373,849 A | 12/1994 | Aldrich | |
| 5,375,602 A | 12/1994 | Bom | |
| 5,453,575 A | 9/1995 | Eberle | |
| 5,423,806 A | 10/1995 | Dale | |
| 5,454,809 A | 10/1995 | Janssen | |
| 5,704,361 A | 1/1998 | Seward | |
| 5,873,835 A | 2/1999 | Hastings | |
| 6,022,309 A * | 2/2000 | Celliers ............... | A61B 18/26 600/7 |
| 6,106,476 A | 8/2000 | Corl | |
| 6,134,003 A | 10/2000 | Boppart | |
| 6,210,404 B1 * | 4/2001 | Shadduck .......... | A61B 18/1492 606/34 |
| 6,421,164 B2 | 7/2002 | Tearney | |
| 6,457,365 B1 | 10/2002 | Stephens | |
| 6,551,250 B2 | 4/2003 | Khalil | |
| 6,659,957 B1 | 12/2003 | Vardi | |
| 6,673,064 B1 | 1/2004 | Rentrop | |
| 6,780,157 B2 | 8/2004 | Stephens | |
| 6,866,670 B2 | 3/2005 | Schellin | |
| 6,969,293 B2 | 11/2005 | Thai | |
| 7,447,388 B2 | 11/2008 | Bates | |
| 7,527,594 B2 | 5/2009 | Vardi | |
| 7,660,492 B2 | 2/2010 | Bates | |
| 7,736,317 B2 | 6/2010 | Stephens | |
| 7,783,337 B2 | 8/2010 | Chen | |
| 7,787,127 B2 | 8/2010 | Galle | |
| 7,995,210 B2 | 8/2011 | Bouma | |
| 7,999,938 B2 | 8/2011 | Wang | |
| 8,059,923 B2 | 11/2011 | Bates | |
| 8,108,030 B2 | 1/2012 | Castella | |
| 8,167,831 B2 | 5/2012 | Wilson | |
| 8,467,831 B2 * | 6/2013 | Camilleri ............... | H04W 8/183 455/428 |
| 2001/0051784 A1 | 12/2001 | Brisken | |
| 2002/0045890 A1 | 4/2002 | Celliers et al. | |
| 2003/0220568 A1 | 11/2003 | Hansmann et al. | |
| 2005/0096647 A1 | 5/2005 | Steinke et al. | |
| 2005/0249391 A1 | 11/2005 | Kimmel | |
| 2006/0206028 A1 | 9/2006 | Lee et al. | |
| 2007/0232933 A1 | 10/2007 | Gille | |
| 2008/0119739 A1 | 5/2008 | Vardi | |
| 2008/0180683 A1 | 7/2008 | Kemp | |
| 2008/0291463 A1 | 11/2008 | Milner | |
| 2009/0043191 A1 | 2/2009 | Castella | |
| 2009/0195514 A1 | 8/2009 | Glynn | |
| 2009/0284332 A1 | 11/2009 | Moore | |
| 2010/0087732 A1 | 4/2010 | Eberle | |
| 2010/0152717 A1 | 6/2010 | Keeler | |
| 2010/0204642 A1 | 8/2010 | Wilson et al. | |
| 2010/0220334 A1 | 9/2010 | Condit | |
| 2011/0125164 A1 | 5/2011 | Nita | |
| 2011/0152771 A1 | 6/2011 | Milner | |
| 2012/0108943 A1 | 5/2012 | Bates | |
| 2012/0232326 A1 | 9/2012 | Habib | |
| 2012/0271170 A1 | 10/2012 | Emelianov | |
| 2013/0023897 A1 | 1/2013 | Wallace | |
| 2013/0223789 A1 | 8/2013 | Lee | |

* cited by examiner

METHODS AND DEVICES FOR THROMBUS DISPERSAL

RELATED APPLICATION

This application is the U.S. National Phase Application under 35 U.S.C. 0 371 of International Application No. PCT/US2014/066112, filed on Nov. 18, 2014, which claims the benefit of and priority to U.S. Provisional No. 61/905,426, filed Nov. 18, 2013. These applications are hereby incorporated by reference herein.

TECHNICAL FIELD

The present invention generally relates to an apparatus and method for dissolution of thrombi and other vessel blockages within the vasculature.

BACKGROUND

Thrombosis is a medical condition that results from the formation of a blood clot, or thrombus, within a vessel. Thrombi often develop in the valves, legs, or other lower abdomen (i.e. deep vein thrombosis), but may occur in other vessels. The clot is typically formed from a pooling of blood within a vein due to abnormally long periods of rest, e.g. when an individual is bed ridden following surgery or suffering a debilitating illness. In addition to thrombosis, atherosclerosis is another medical condition that results from the formation of a blockage in a vein. Atherosclerosis is due to the build of atheroma material along the arterial walls. Atheroma deposits can have widely varying properties, with some deposits being relatively soft and others being fibrous and/or calcified. In the latter case, the deposits are frequently referred to as plaque. Often thrombosis and atherosclerosis are both present in the veins. For example, a thrombus develops around the atherosclerotic plaque.

The formation of thrombi and build-up of plaque can lead to a stroke or embolism, which may cause serious health issues, including death. Strokes occur when the blood clot or plaque blocks an artery supplying blood to the brain, thus depriving the brain tissue of oxygen. Without oxygen, brain cells begin to die. Embolisms occur when a blood clot travels around the body and lodges itself in an organ. For example, a pulmonary embolism is a blockage of the blood supply to the lungs that causes severe hypoxia and cardiac failure.

For some blockages, surgical intervention with ultrasonic catheters may be necessary to remove the thrombus, plaque, or both from a vessel, such as when cholesterol or anti-coagulant medications are not able to reduce the blockage. Ultrasonic catheters for dissolution of blockages are described in, for example, U.S. Pat. Nos. 6,969,293 and 6,866,670. Removal of blockages with ultrasonic energy alone, however, often fails to completely disperse the blockage within the vessel. Rather, more complete dissolution often requires withdrawal of the ultrasonic catheter from the vessel and the introduction of one or more other catheters to finalize the clot dissolution procedure. The multiple catheter exchanges may be injurious to the patient because the blood vessel interior is delicate, may be weakened by disease, and is therefore susceptible to injury from movement of the catheter body within it. As such, the need to move a catheter, let alone multiple catheters, within the patient should be minimized.

SUMMARY

The invention recognizes that current blockage dissolution procedures often require exchanging multiple catheters in order fully treat a blood vessel. Catheter systems and methods of the invention provide for a more complete dissolution within a vessel while minimizing the number of catheters that are introduced into the vessel. This reduces the risk associated with exchanging and moving multiple catheters within the delicate vasculature that may be weakened by disease. Aspects of the invention are accomplished by providing a catheter system that includes an acoustic energy source disposed within a catheter body and at least one other dissolution element operably associated with the catheter body. While the energy source acts to dissolve the blockage through use of high frequency acoustic waves, the at least one other dissolution element works to dissolve or minimize the occlusion in another manner. According to certain embodiments, the dissolution element is a balloon, heating element, steam, or combination thereof.

Catheter systems of the invention include an elongate body and an inner member configured for insertion into a lumen of the elongate body. The inner member includes an acoustic energy source configured to deliver therapeutic energy to a treatment site (e.g. occlusion) within the blood vessel. The occlusion may include a thrombus, atheroma material, or a combination thereof. The therapeutic energy applied to the treatment site is ideally configured to dissolve the occlusion within the blood vessel, while avoiding damage to healthy surrounding tissue. In addition to the acoustic energy source, the catheter system includes at least one other dissolution element to ensure maximum dissolution of the blockage during the intraluminal procedure. In certain embodiments, the at least one other dissolution element is configured to directly contact the occlusive material such that blockage is dispersed in a controlled manner.

Typically, the energy source of the inner member is an acoustic energy source. The acoustic energy source may be an ultrasound transducer array disposed within the inner member. The acoustic energy source is configured to deliver the therapeutic energy within a blood vessel. In certain embodiments, the therapeutic energy is ultrasonic, but other levels of acoustic energy may be administered as appropriate for the desired treatment. The therapeutic energy may be consistent applied or intermittently applied to the treatment site. During application of the therapeutic energy, the inner member may be translated longitudinally within the elongate body or rotated within the elongate body.

In particular embodiments, the dissolution element of the catheter system is a balloon. The balloon may be located on a distal portion of the elongate body. For example, the balloon may be inflated within the vessel in order to compress any remaining occluded material after application of the acoustic energy. The compression of plaque increases blood flow within the vessel. Additionally or in the alternative, the catheter system may include one or more heating elements. The heating elements may act to directly apply heat, such as ablative heat, to the blockage in a controlled and contained manner. For example, heating elements may act to only ablate and remove occlusive material in direct contact with the heating elements. The heating elements may be located along the length of the elongate body of the catheter system or on the distal end of the catheter system. Heating elements located on the distal end advantageously allow one to ablate the blockage located in front of the catheter system. Suitable heating elements include electrodes and/or lasers. Lasers may be formed from one or more optical fibers disposed within a second lumen of the elongate body. The one or more optical fibers preferably include an active end that is located on the distal end of the elongate body.

Additionally, catheter systems of the invention may emit steam as the dissolution element. In such embodiments, the elongate body includes one or more steam lumens that are coupled to one or more steam exit ports located on the elongate body. A steam source is operably associated with the elongate body and configured to transmit steam through the steam lumens and out of one or more steam exit ports. The steam assists in softening the thrombi and also acts to mechanically break down the blockage. In certain embodiments, the steam includes a thrombolytic agent.

In some aspects, a catheter system of the invention for delivering therapy includes an elongate body defining a first lumen and comprising a distal portion, an opening along a side of the distal portion and associated with the first lumen, and a steam source operably associated with the first lumen, and configured to deliver steam through the opening of the first lumen and to a treatment site.

DETAILED DESCRIPTION

Catheter systems of the invention are designed to deliver therapeutic energy within a body lumen to dissolve a blockage. According to certain embodiments, catheter systems include an energy source disposed within a catheter body and configured to emit therapeutic acoustic energy to a treatment site. In certain embodiments, the catheter systems also include one more dissolution elements that act to assist the acoustic energy in removing/minimizing the blockage. The combination of an acoustic energy source and at least one other dissolution element in a single catheter system provides for a more complete dissolution procedure while minimizing the number of catheters that are introduced into the vessel. This reduces risk associated with exchanging and moving multiple catheters within the delicate vasculature that may be weakened by disease.

As discussed, catheter systems of the invention include an acoustic energy source in combination with one or more other dissolution elements. In addition to those features, the catheter systems may also include one or more imaging elements, one or more functional flow elements, one or more cooling elements, or combinations thereof. As described herein, the various additional embodiments of the catheter systems can be used in combination with each other. For example, the catheter systems may include imaging elements, functional flow elements, cooling elements, heating elements and any combination thereof.

Figure 1:
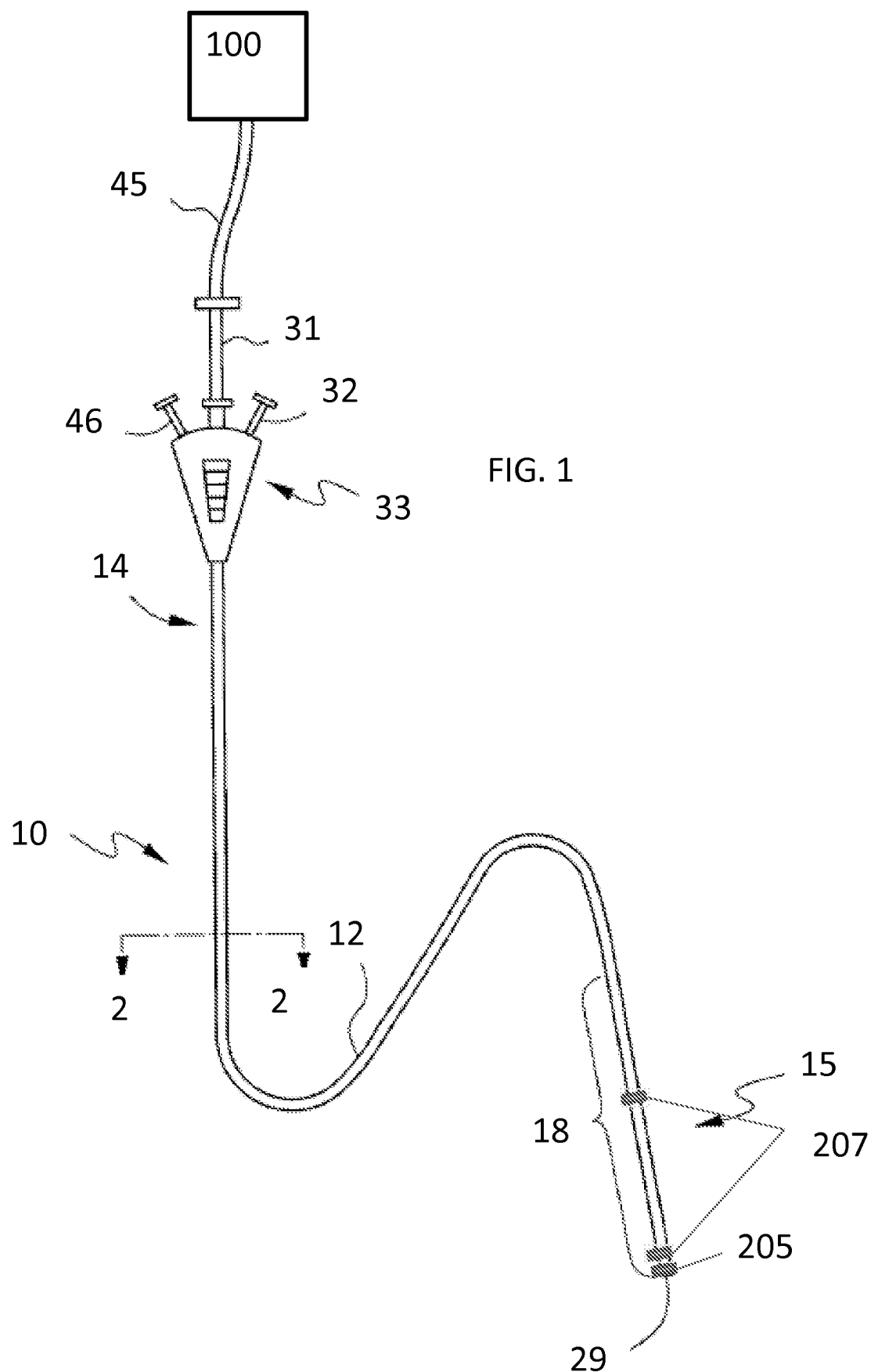
FIG. 1 is a schematic illustration of a catheter system of the invention according to certain embodiments.

As illustrated in FIG. 1, the catheter system 10 of the invention generally comprises a multi-component, tubular body 12 having a proximal region 14 and a distal region 15. The tubular body 12 includes a flexible energy delivery section 18 and a distal exit port 29 located in the distal region 15 of the catheter 10. A backend hub 33 is attached to the proximal region 14 of the tubular body 12, the backend hub 33 comprising a proximal access port 31, an inlet port 32 and a cooling fluid fitting 46. The proximal access port 31 can be connected to control circuitry 100 via cable 45. The tubular body 12 defines one or more lumens (e.g. a lumen to receive an energy source, an imaging lumen, or a fluid delivery lumen).

The tubular body 12 and other components of the catheter system 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, nickel titanium or stainless steel wires can be placed along or incorporated into the tubular body 12 to reduce kinking.

The width dimensions (e.g. diameter) of the tubular body 12 may vary depending on the application (e.g. arteries, veins, capillary). For example, the tubular body 12 may be designed to fit into a vessel containing a blockage. In an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths may by appropriate for other applications. The tubular body 12 is not limited to a tubular shape, and may be any other shape suitable for insertion into vessels of the body.

The energy delivery section 18 of the tubular body 12 preferably comprises a material that is thinner than the material comprising the proximal region 14 of the tubular body 12 or a material that has a greater acoustic transparency. Thinner materials generally have greater acoustic transparency than thicker materials. Suitable materials for the energy delivery section 18 include, but are not limited to, high or low density polyethylenes, urethanes, nylons, and the like. In other embodiments, the energy delivery section 18 may be formed from the same material or a material of the same thickness as the proximal region 14.

The distal region 15 of the tubular body 12 may include one or more imaging elements 205 and/or one or more functional flow elements 207. In certain embodiments, the functional flow elements 207 are positioned on the tubular body 12 such that one functional flow element 207 is distal to another functional flow element 207. This allows one to determine differences in blood pressure and flow across the length of the vessel. Functional flow elements and methods of using information obtained from functional flow elements 207 is described in more detail hereinafter. The imaging elements 205 may partially surround or completely surround the tubular body 12. When completely surrounding the tubular body 12, the imaging elements 205 provide for circumferential imaging of the body lumen.

The material of the tubular body 12 may be of variable thickness from the proximal portion to the distal portion. The variable thickness may be gradual or segmented. In certain embodiments, the tubular body 12 is divided into at least three sections of varying stiffness. The first section, which preferably includes the proximal region 14, has a relatively higher stiffness. The second section, which is located in an intermediate region between the proximal region 14 and the distal region 15 of the tubular body 12, has a relatively lower stiffness. This configuration further facilitates movement and placement of the catheter system 10. The third section, which preferably includes the energy delivery section 18, generally has a lower stiffness than the second section.

Figure 2:
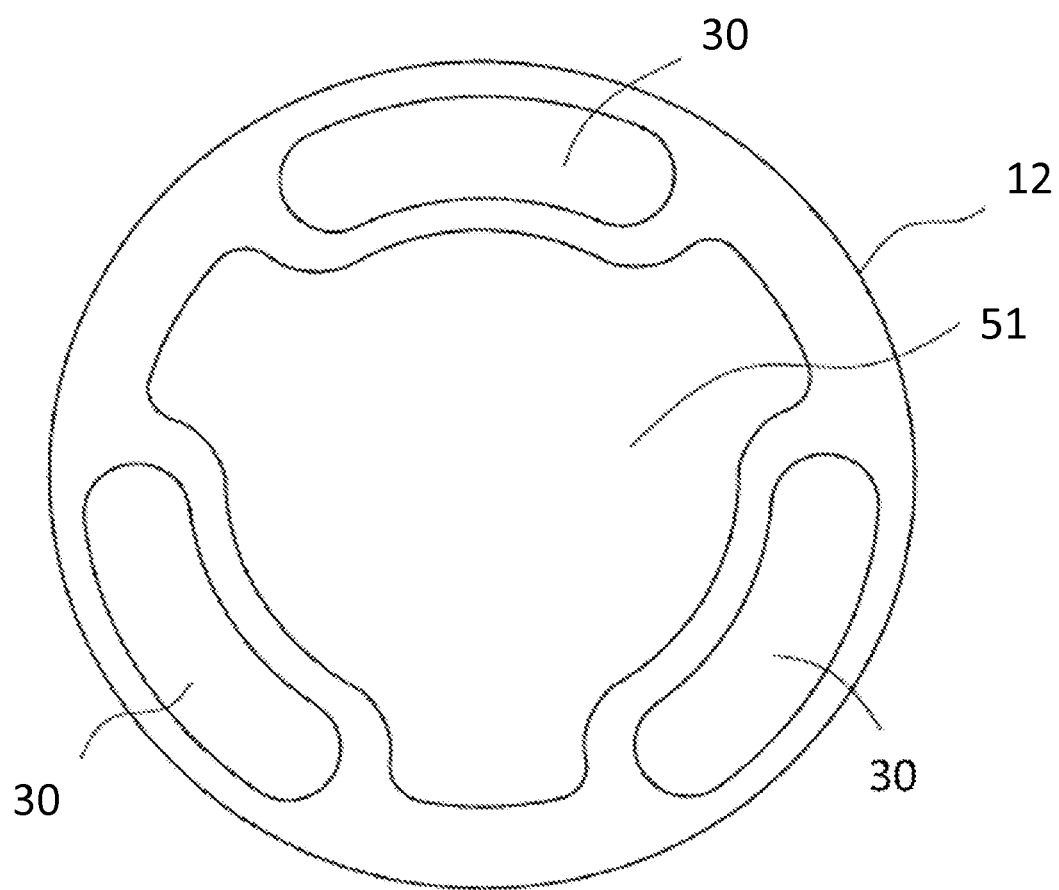
FIG. 2 illustrates a cross-section of the catheter system according to one embodiment.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The fluid delivery lumens are configured to deliver drugs to the treatment site (e.g. anti-coagulation drugs) and may also act to cool the energy source. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub 33 preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3A:
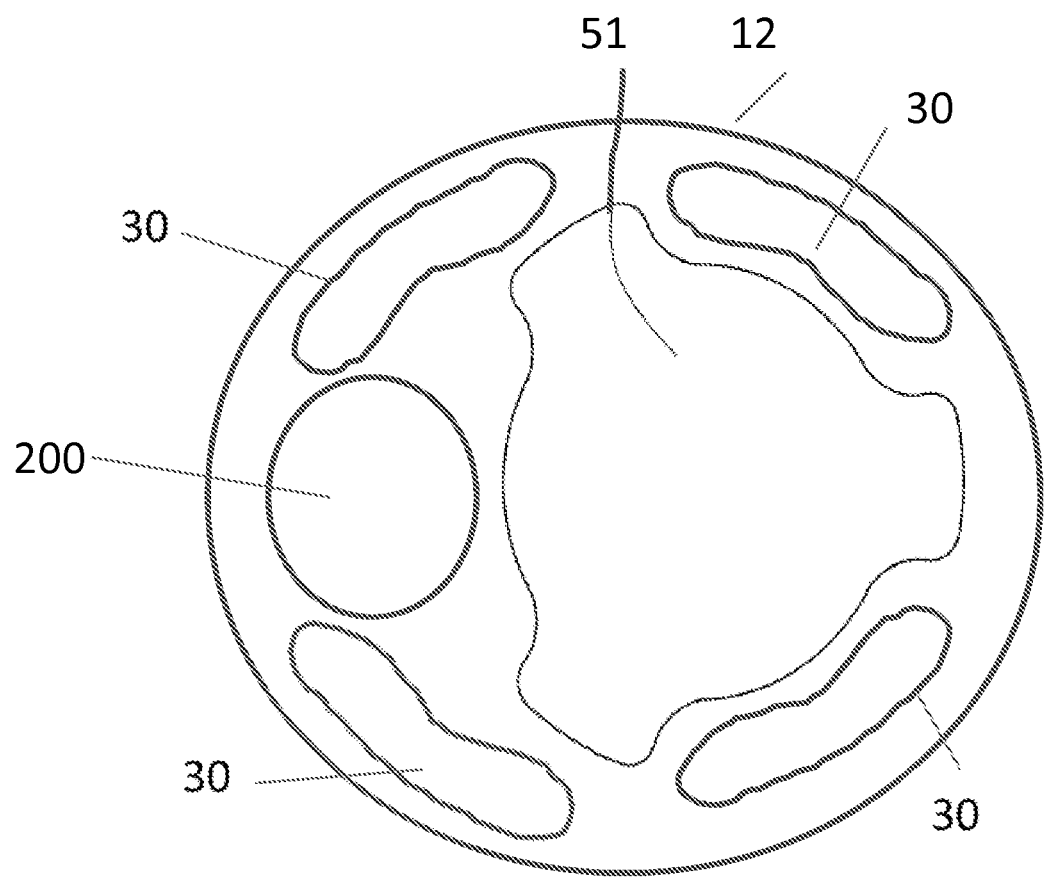
FIG. 3A illustrates a cross-section of the catheter system according to another embodiment.
Figure 3B:
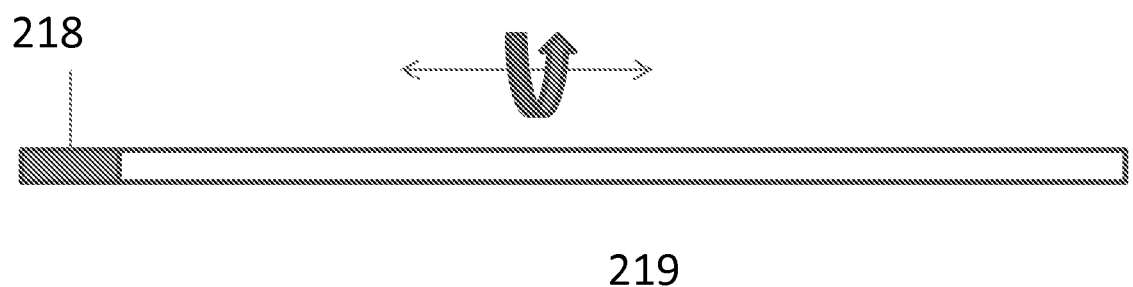
FIG. 3B illustrates an imaging member for use with the catheter system of FIG. 3A.

FIG. 3A illustrates a cross-section of the tubular body 12 taken along line 2-2 in FIG. 1, according to another embodiment. As shown in FIG. 3A, the tubular body 12 further includes an imaging lumen 200 configured to receive a device for imaging the body lumen. For example, one or more imaging elements 218 operably associated with an elongate member 219, such as a drive shaft, can be introduced into the imaging lumen 200. The elongate member 219 and one or more imaging elements 218 are shown in FIG. 3B. The imaging element(s) 218 may be translated longitudinally and/or rotated within the imaging lumen 200. The imaging element(s) 218 can partially surround or completely surround the elongate member 219. When the imaging elements 218 completely surround the elongate member 219 they can provide circumferential imaging of the body lumen without the need for rotation. Alternatively, the imaging elements 218 may only partially surround the elongate member 219, and in such embodiments, the elongate member 219 may be rotated to provide circumferential imaging. The types of imaging elements are described in more detail hereinafter. In certain embodiments, the elongate member 219 is moveable beyond the distal end of the tubular body 12 through an exit port associated with the imaging lumen 200. This allows imaging element 218 to image beyond the distal end of the tubular body 12, and advantageously allows the imaging element to obtain images in regions of the vessel where the tubular body 12 may not fit because of its size.

Figure 4:
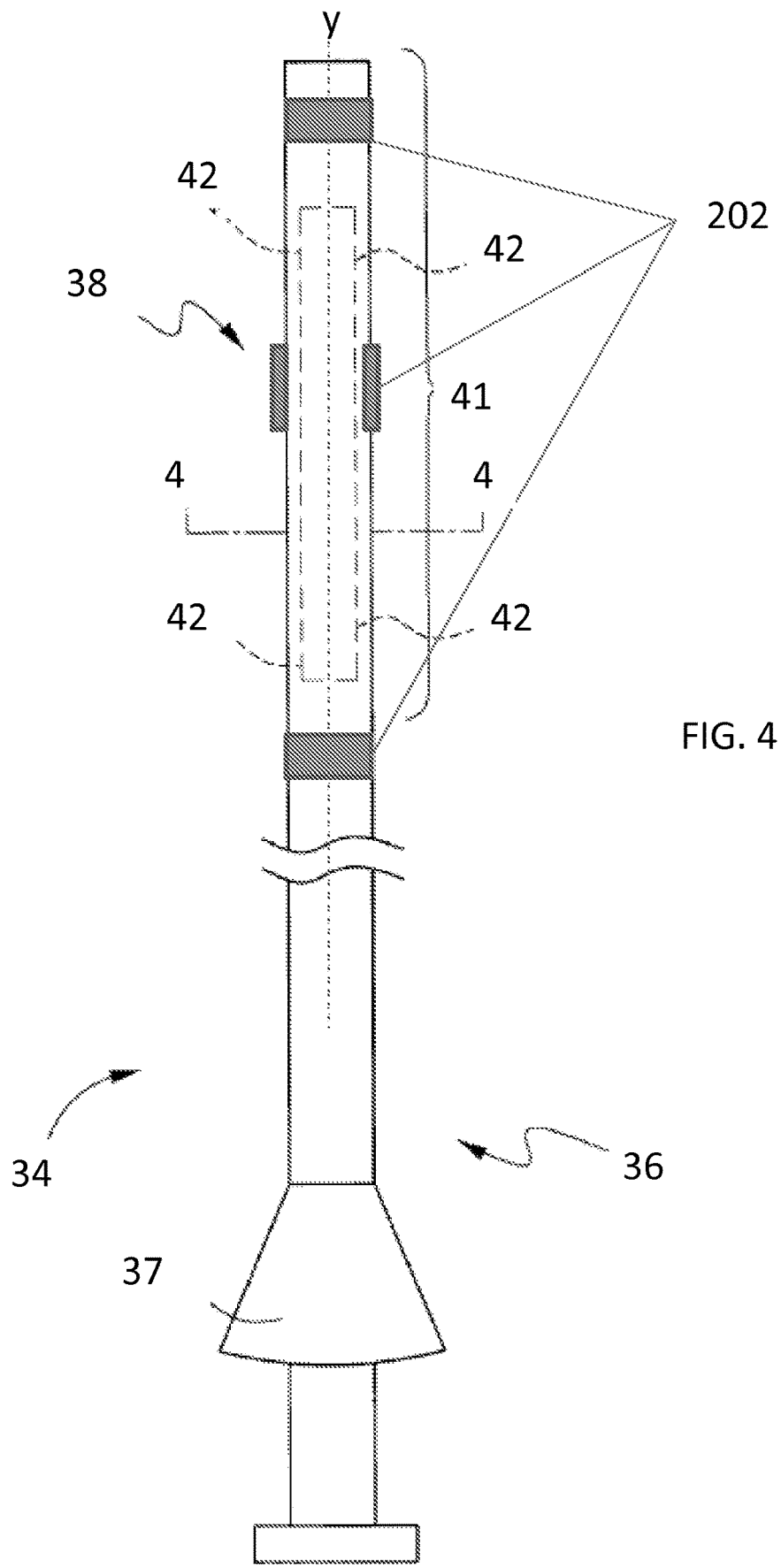
FIG. 4 illustrates an inner core of the catheter system according to certain embodiments.

The central lumen 51 is configured to receive an elongate inner core 34, such as illustrated in FIG. 4. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members form an ultrasound assembly 42 for generating energy that breaks down the blockage within the vessel, which will be described in greater detail below. As shown in FIG. 4, the elongate inner core 34 may also include one or more imaging elements 202. The imaging elements can be used to image the vessel surface in order to guide placement of the inner core energy delivery section 41 at the treatment site. The imaging elements 202 can partially surround or completely surround the body of the elongate inner core 34. When the imaging elements 202 completely surround the elongate body of the inner core 34 they can provide circumferential imaging of the body lumen without rotation. Alternatively, the elongate inner core 34 can be configured to rotate, and in such aspect, imaging elements partially surrounding the inner core may also be used to provide circumferential imaging of the body lumen as the elongate inner core 34 rotates. The imaging elements 202 can also be used to survey the treatment site after application of energy (e.g. ultrasonic) to dissolve the blockage.

Figure 5:
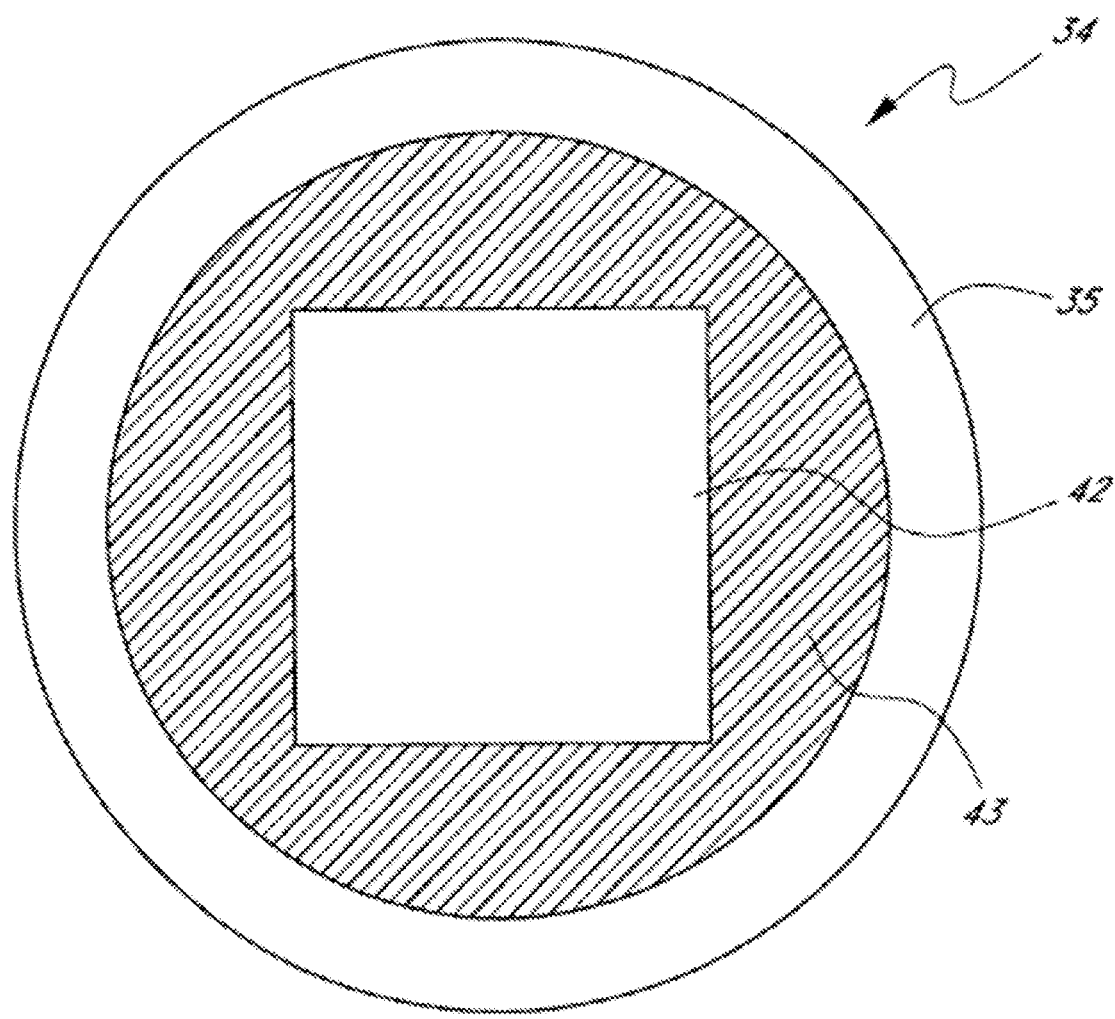
FIG. 5 illustrates a cross-section of the inner core according to certain embodiments.

As shown in the cross-section illustrated in FIG. 5, which is taken along lines 4-4 in FIG. 4, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 5, the inner core 34 preferably comprises a cylindrical outer body 35 that houses the ultrasound assembly 42. The ultrasound assembly 42 comprises wiring and ultrasound radiating members, described in greater detail in FIGS. 6 through 8D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to control circuitry 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. However, the ultrasound assembly 42 may be secured within the inner core in any suitable manner. For example, the ultrasound assembly 42 may be secured to a luminal inner surface of the cylindrical outer body 35 of the inner core 34. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

In embodiments where the inner core 34 includes one or more imaging elements 202, the wiring of the imaging elements 202 that connects the imaging elements 202 to an imaging system can be disposed within the electrically-insulating potting material or a lumen of the inner core 34.

Figure 6:
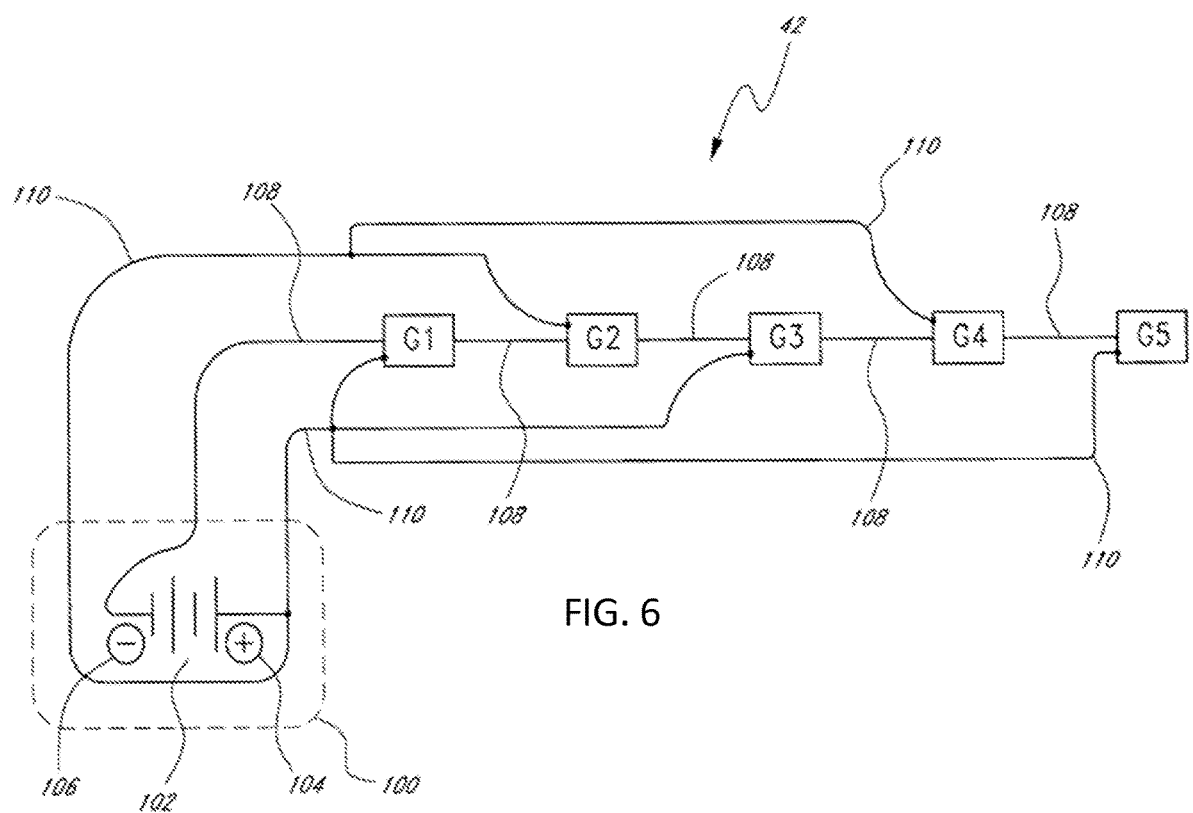
FIG. 6 illustrates control circuitry of an ultrasound assembly for use with the catheter systems of the invention.
Figure 7:
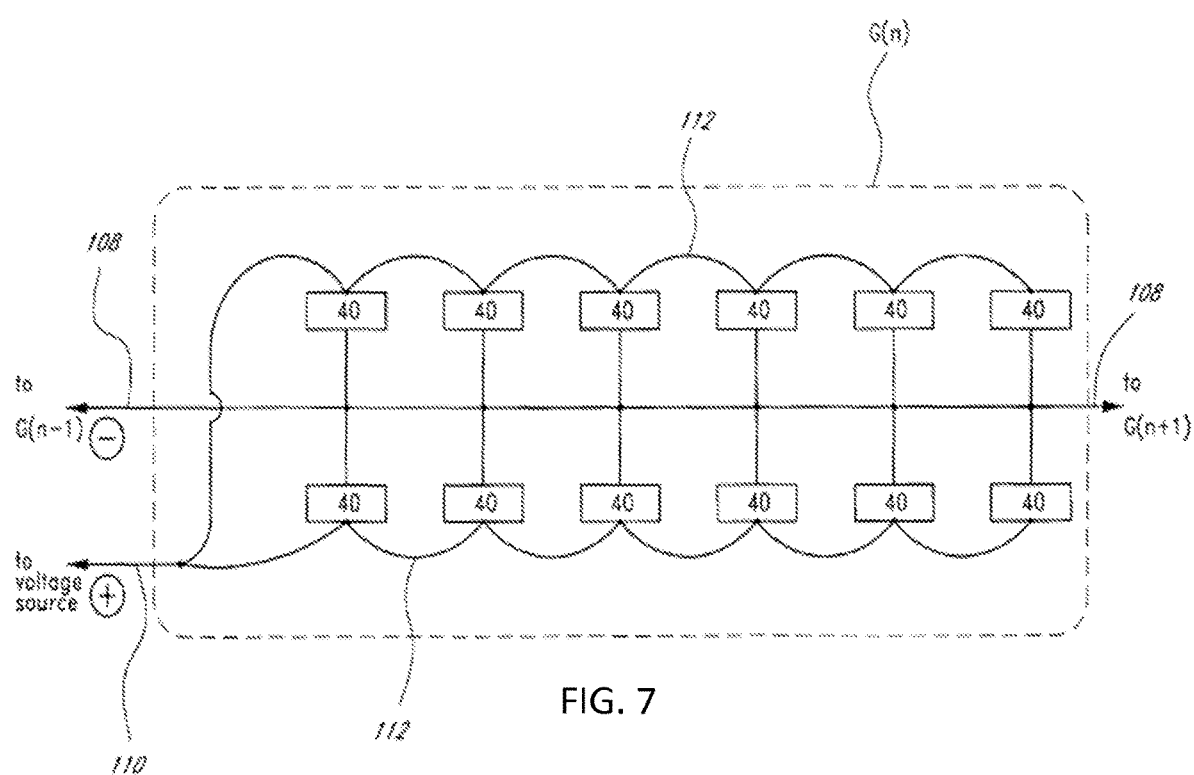
FIG. 7 illustrates other control circuitry of an ultrasound assembly for use with the catheter system of the invention according to certain embodiments.

In a preferred embodiment, the ultrasound assembly 42 comprises a plurality of ultrasound radiating members that are divided into one or more groups. For example, FIGS. 6 and 7 are schematic wiring diagrams illustrating one technique for connecting five groups of ultrasound radiating members 40 to form the ultrasound assembly 42. As illustrated in FIG. 6, the ultrasound assembly 42 comprises five groups G1, G2, G3, G4, G5 of ultrasound radiating members 40 that are electrically connected to each other. The five groups are also electrically connected to the control circuitry 100.

The ultrasound assembly 42 transmits ultrasound energy transferred through longitudinal pressure or compression waves for treatment of the blockage. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts. The amount of ultrasound energy used for blockage dissolution may be different from the amount ultrasound energy that an ultrasound imaging element utilizes to image the luminal surface.

Ultrasound radiating members of the ultrasound assembly 42 may include any apparatus capable of producing ultrasonic energy for therapeutic purposes. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 6, the control circuitry 100 preferably comprises, among other things, a voltage source 102. The voltage source 102 comprises a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 7, is connected to the positive terminal 104 via one of the lead wires 110, and to the negative terminal 106 via the common wire 108.

Referring now to FIG. 7, each group G1-G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 7 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 6.

Figure 8A:
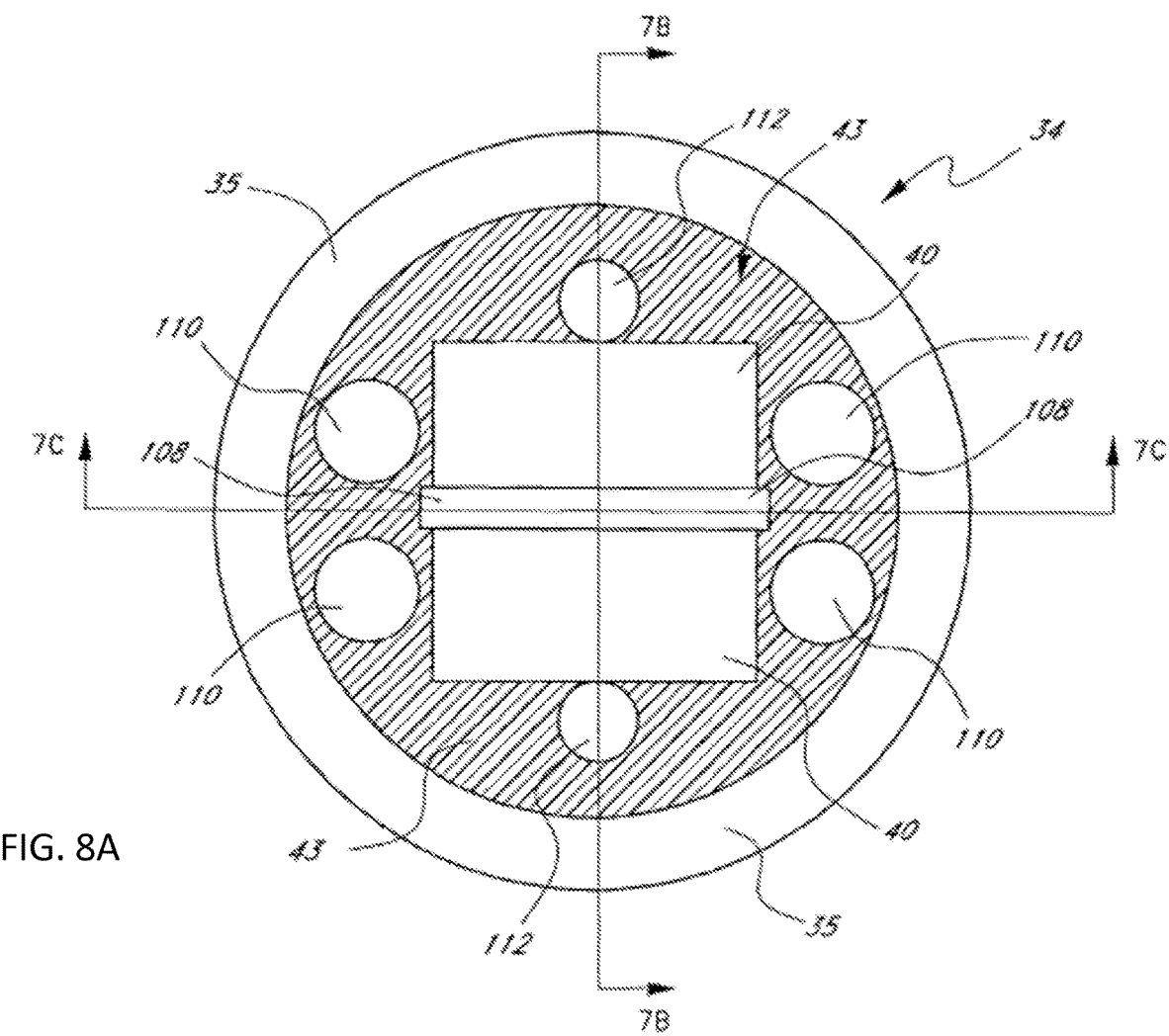
FIGS. 8A-8C illustrate various cross-sections of the inner core and ultrasound assembly according to certain embodiments.

FIG. 8A illustrates one preferred technique for arranging the components of the ultrasound assembly 42 (as schematically illustrated in FIG. 5) into the inner core 34 (as schematically illustrated in FIG. 4). FIG. 8A is a cross-sectional view of the ultrasound assembly 42 taken within group G1 in FIG. 6, as indicated by the presence of four lead wires 110. For example, if a cross-sectional view of the ultrasound assembly 42 was taken within group G4 in FIG. 6, only one lead wire 110 would be present (that is, the one lead wire connecting group G5).

Referring still to FIG. 8A, the common wire 108 comprises an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

Figure 8B:
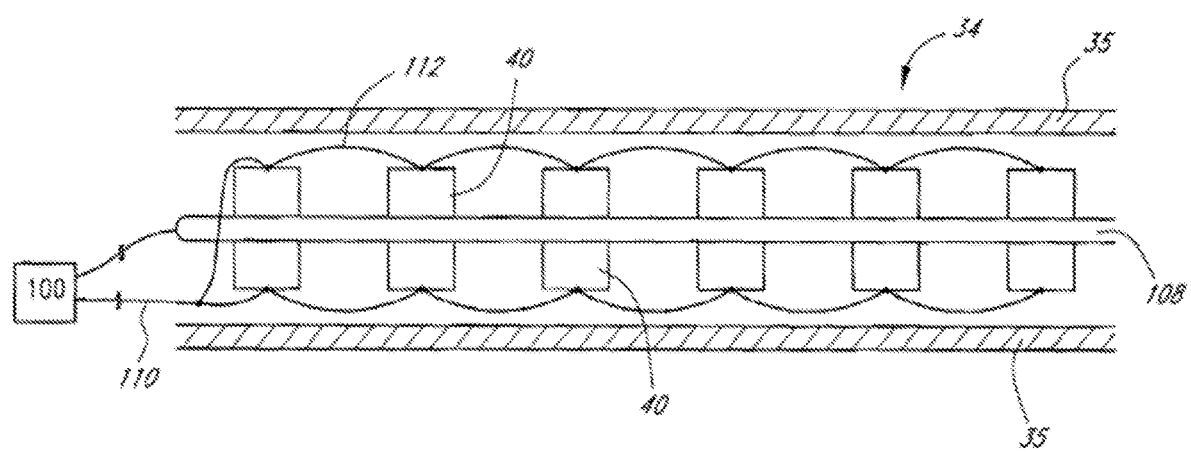
Figure 8C:
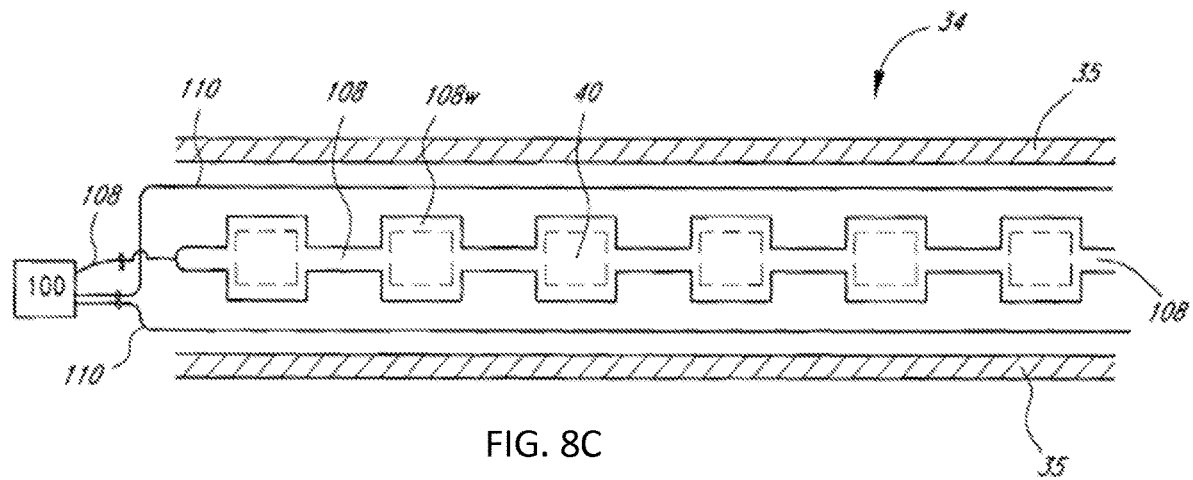

FIGS. 8B and 8C illustrate cross sectional views of the inner core 34 of FIG. 8A taken along lines 7B-7B and 7C-7C, respectively. As illustrated in FIG. 8B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 8C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 8D:
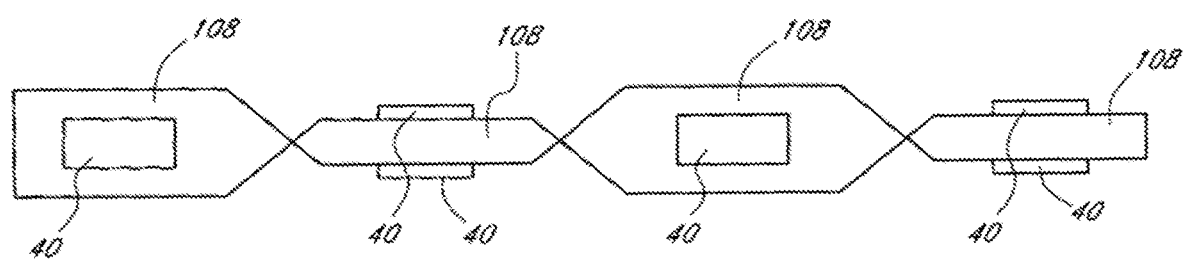
FIG. 8D illustrates another configuration of the ultrasound assembly.

In a modified embodiment, such as illustrated in FIG. 8D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 6 through 8, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focused, more diffuse ultrasonic energy field to the treatment site.

In a preferred embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36-gauge electrical conductors, while positive contact wires 112 are preferably 42-gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment the frequency is between about 1 MHz and 3 MHz. In yet another embodiment, the ultrasound radiating members 40 are operated with a frequency of about 2 MHz.

Figure 9A:
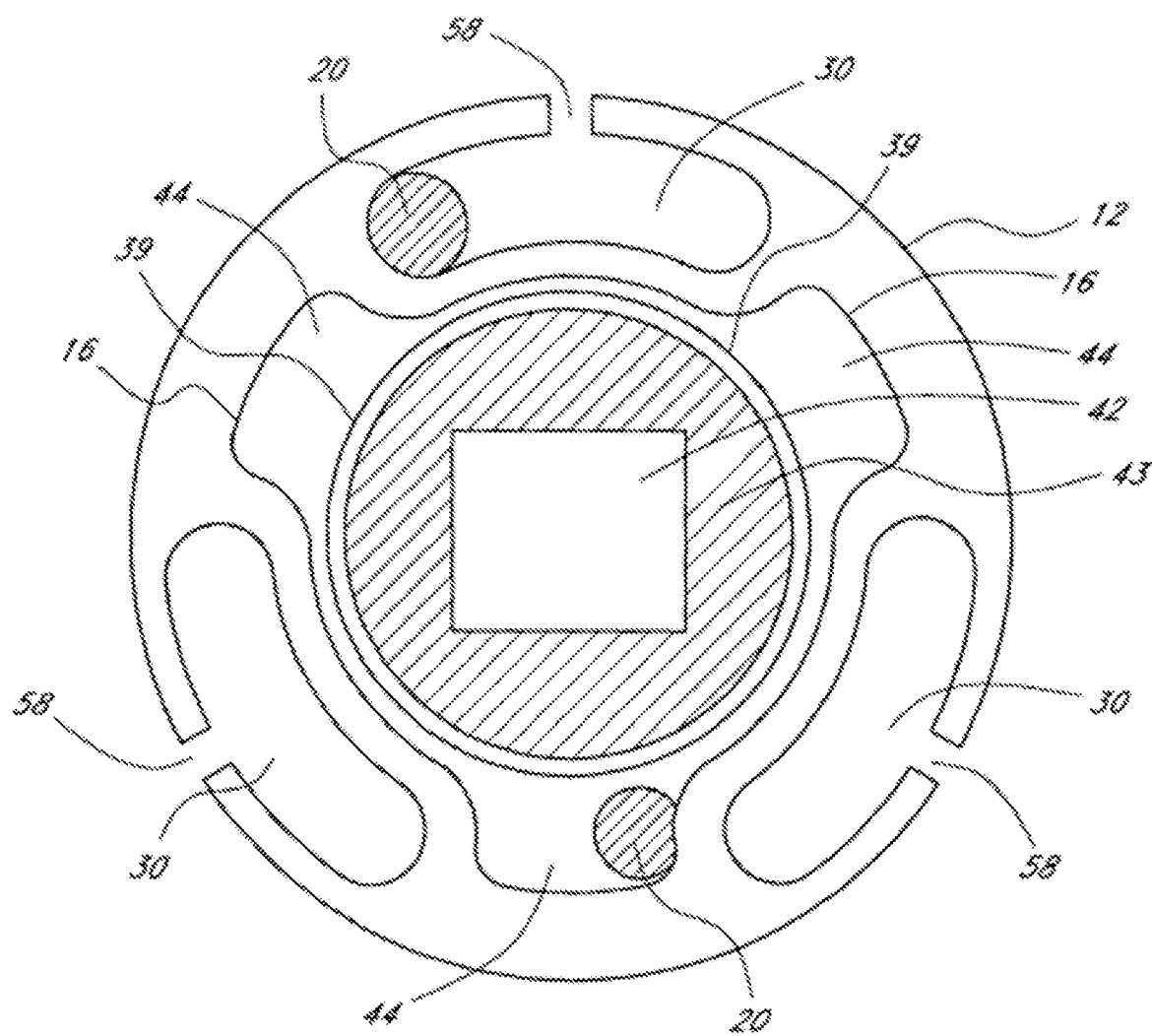
FIGS. 9A-9C illustrates cross-sections of the catheter system according to various embodiments.

In practice, the tubular body 12 receives the elongate inner core 34 through the central lumen 51. FIG. 9A illustrates the inner core 34 positioned within the tubular body 12. Details of the ultrasound assembly 42, provided in FIG. 8A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

Figure 12A:
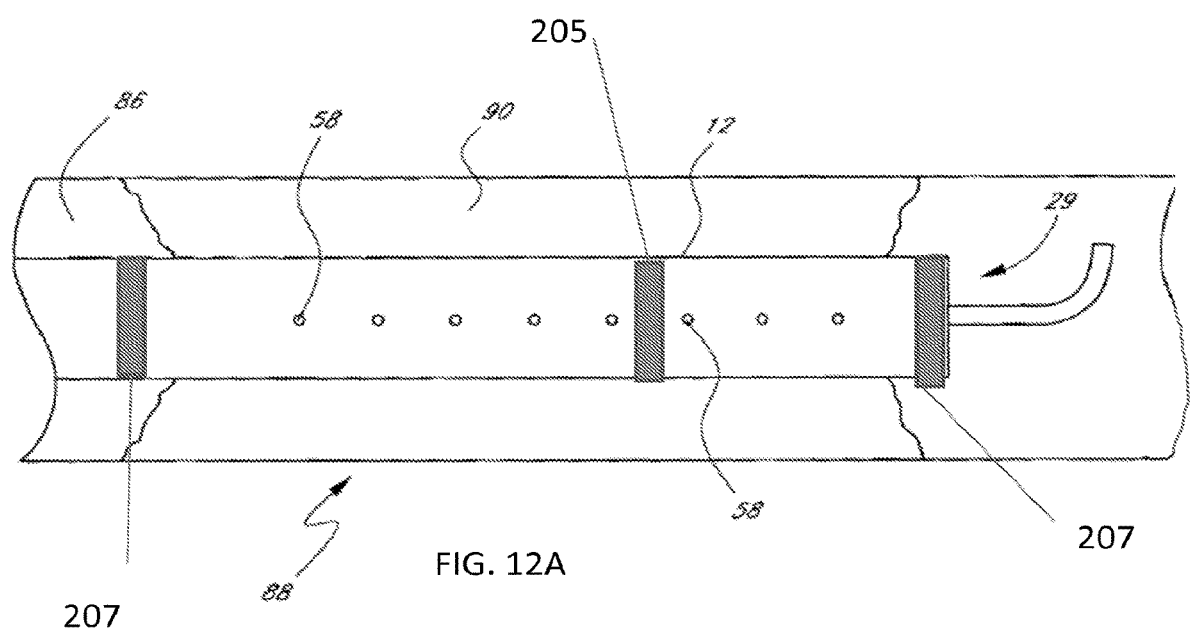
FIGS. 12A-12C provide a schematic illustration of the catheter system as used in a clot dissolution procedure.
Figure 12B:
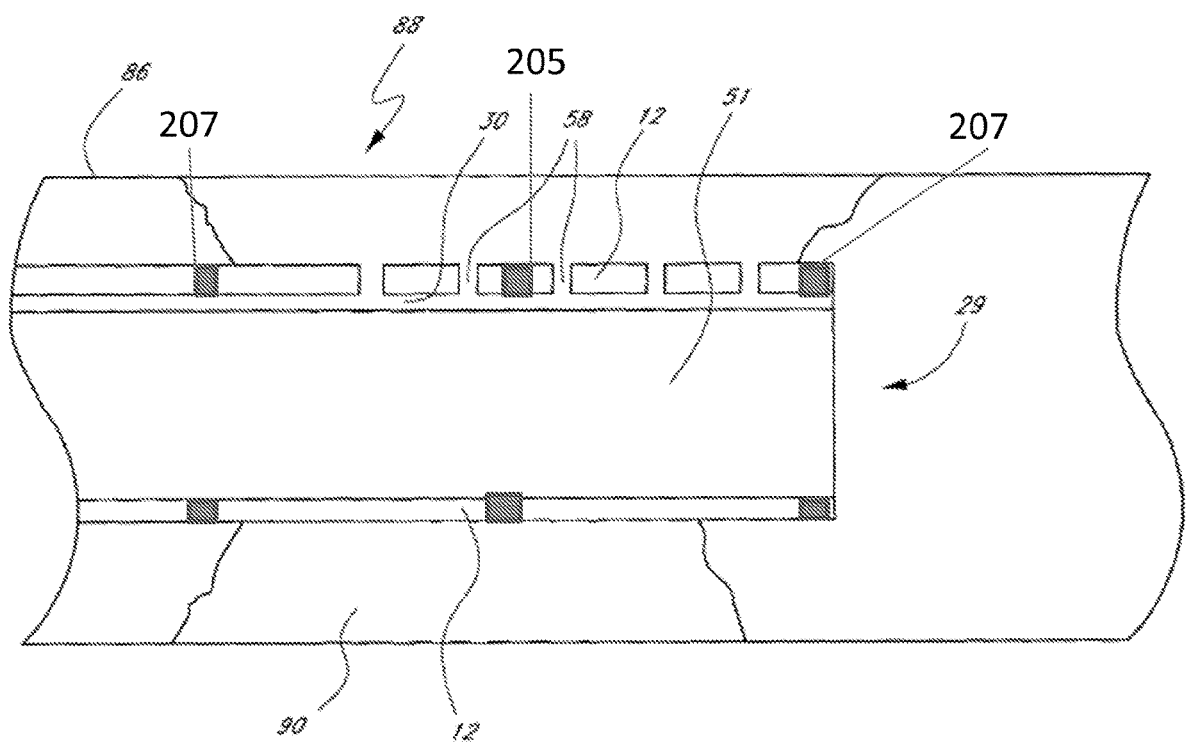

FIG. 9A further illustrates placement of fluid delivery ports 58 within the tubular body energy delivery section 18 (see also FIG. 12B to view the fluid delivery ports). As illustrated, holes or slits are formed from the fluid delivery lumen 30 through the tubular body 12, thereby permitting fluid flow from the fluid delivery lumen 30 to the treatment site. The fluid delivery ports allow drugs and other therapeutic compounds to be delivered directly into the treatment site. Thus, a source of therapeutic compound coupled to the inlet port 32 provides a hydraulic pressure which drives the therapeutic compound through the fluid delivery lumens 30 and out the fluid delivery ports 58.

The fluid delivery ports 58 and fluid delivery lumens 30 can be arranged in several different configurations. By evenly spacing the fluid delivery lumens 30 around the circumference of the tubular body 12, as illustrated in FIG. 9A, a substantially even flow of therapeutic compound around the circumference of the tubular body 12 can be achieved. In addition, the size, location and geometry of the fluid delivery ports 58 can be selected to provide uniform fluid flow from the fluid delivery lumen 30 to the treatment site. For example, in one embodiment, fluid delivery ports 58 closer to the proximal region of the energy delivery section 18 have smaller diameters than fluid delivery ports 58 closer to the distal region of the energy delivery section 18, thereby allowing uniform delivery of fluid across the entire energy delivery section 18.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12. It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 9A, placement of the inner core 34 within the tubular body 12 further defines one or more cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120° increments for a three-lumen configuration), thereby providing uniform cooling fluid flow over the inner core 34. Such a configuration is desired to remove unwanted thermal energy at the treatment site. As will be explained below, the flow rate of the cooling fluid and the power to the ultrasound assembly 42 can be adjusted to maintain the temperature of the inner core energy delivery section 41 within a desired range.

In a preferred embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

When the inner core 34 rotates, the rotation likewise causes rotation of the ultrasound assembly 42 disposed within the inner core 34. In doing so, rotation of the inner core 34 causes the plurality of ultrasound radiating members 40 of the ultrasound assembly 42 to emit higher ultrasound energy at higher frequencies than possible without rotation. The higher frequency when rotating increase the ultrasound assembly's ability to drive thrombolytic drugs and other substances into the clot faster than the lower frequencies obtained from stationary elements. Rotation of the inner core 34 also enhances imaging obtained from one or more imaging elements 202 located on the inner core because rotation of the imaging elements 202 increases the resolution of the obtained imaging data and allows for circumferential imaging of the luminal surface. In these rotational embodiments, the signal wires of the ultrasound assembly, imaging elements, and functional flow elements (that connect the ultrasound assembly, functional flow elements, imaging elements to power sources and control systems) may be coupled to an optical and/or electrical rotary joint. Rotary joints provide for distal rotation of the signal wire coupled to ultrasound assembly, imaging elements, and functional flow elements while the proximal portion of the signal wire is coupled to the power sources and control systems maintains stationary. Electrical and optical rotary joints are known in the art. See, for example, co-owned US Patent Publication No. 20130223789 for an exemplary optical rotary joint.

In certain embodiments, the ultrasound assembly 42 is associated with one or more cooling elements to effectuate cooling and prevent overheating of the ultrasound assembly 42. The cooling elements can operate in combination with the cooling fluid introduced into the cooling fluid lumens 44, or used as an alternative to the cooling fluid. In one embodiment, a cooling element is coupled to each ultrasound radiating member 40 of the ultrasound assembly 42. Alternatively, a cooling element is coupled to two or more ultrasound radiating members 40 or the entire ultrasound assembly 42, such that the cooling element is shared. In certain embodiments, the cooling element(s) is coupled to a backing of the ultrasound assembly and positioned within the inner core 34 along with the ultrasound assembly 42 and surrounded by the potting material 43. If a potting material is not used to surround the ultrasound assembly 42 (e.g. when the ultrasound assembly 42 is secured against a side of the inner core 42), then the cooling element is coupled to a backing of the ultrasound assembly 42 and disposed within the inner core 34. The cooling element(s) may be a heat sink, a thermoelectric cooler, or combination thereof, which are described in more detail hereinafter.

Heat sinks are passive exchangers that cool a device by dissipating heat into the surrounding medium. According to certain embodiments, the surrounding medium is the insulating potting material 43 of the inner core 34 (for example, when the ultrasound transducer assembly 42 is secured in the insulating potting material 43 as in FIG. 5). Alternatively, the surrounding medium is may be a cooling fluid (for example, when the inner core 34 defines a hollow lumen and the ultrasound assembly 42 is attached to a luminal surface of the inner core or otherwise stabilized/positioned within the distal portion of the inner core). Typically, the cooling fluid is saline.

The heat sink itself may be one or more thermally conductive elements that extend proximally from the distal ultrasound assembly 42 (i.e. from one or more of the ultrasound radiating members 40) along the shaft of the inner core 34. The thermally conductive elements prevent heat from concentrating at the location of the ultrasound radiating members 40, and instead allow heat to travel along the thermal conductive elements and dissipate within the potting material 43 or other dissipating medium (e.g. saline fluid). The thermally conductive elements may extend the entire length of the inner core, or extend a partial length of the inner core.

The thermally conductive elements, according to some embodiments, may include cooling fins. The cooling fins may be attached to the backing of the ultrasound transducer. Cooling fins include one or more surfaces that extend from an object to increase the rate of heat transfer to or from the environment, thereby cooling object through dissipation of heat. Alternatively, the thermally conductive elements include one or more strands of a thermally conductive material. The strands may be braided, wound (such as spiral configuration), or combination of both. Suitable thermally conductive materials include silver, gold, nickel, steel, copper, platinum, and combinations thereof. An advantage of heat sink is the ability to spread concentrated heat from ultrasound assembly and dissipate that heat through a greater area of the catheter.

Figure 15A:
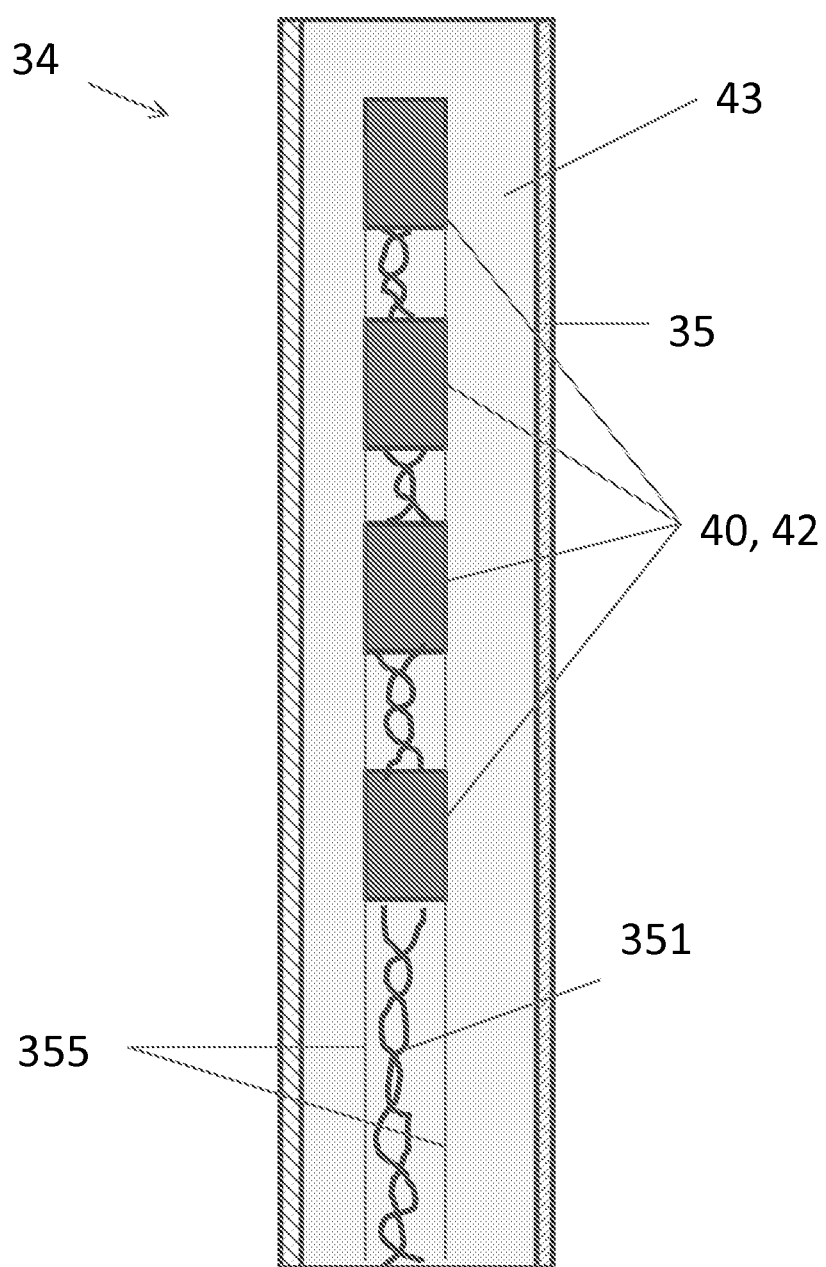
FIGS. 15A-15B illustrate embodiments of the catheter system with a cooling element.
Figures 15B, 16:
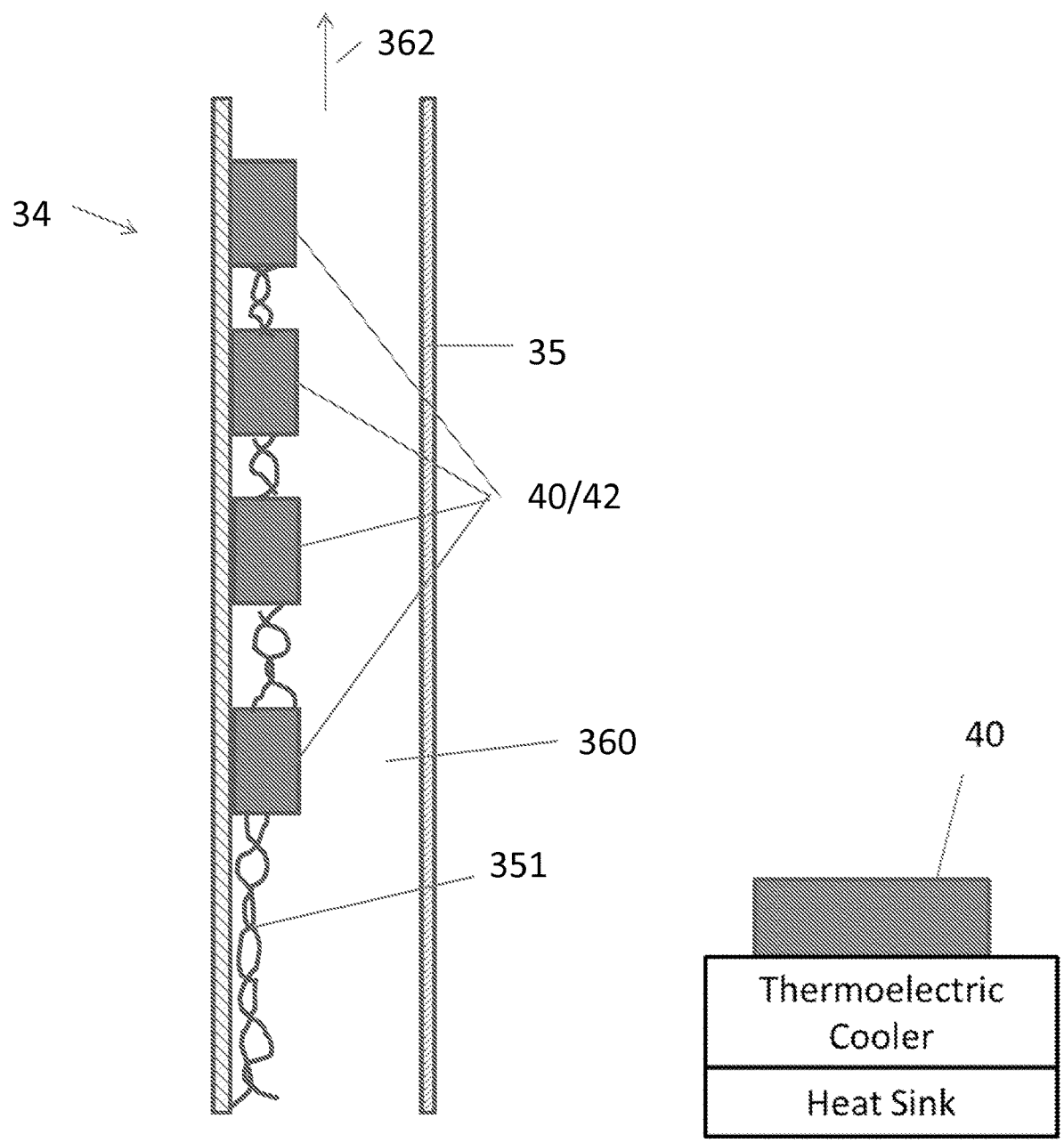
FIG. 16 depicts a simplified diagram of the cooling element formed from both the thermoelectric cooling element in combination with a heat sink.

FIG. 15A shows a cross-section of the inner core 34 along longitudinal line y, as depicted in FIG. 4. As shown in FIG. 15A ultrasound radiating members 40 of the ultrasound assembly coupled to heat sink 351 (shown as braided thermally conductive elements, but the heat sink could alternatively be cooling fins). The heat sink 351 cools the ultrasound transducer assembly 42 by transferring heat from the ultrasound radiating member 40 and through the heat sink 351 that runs proximally along the length of the inner core 34 from the ultrasound radiating members 40. The heat sink 351 may run the entire length of the inner core 34 or partially along the length of the inner core 34. As the heat transfers from the ultrasound radiating members 42 along the length of the heat sink 351, the heat dissipates into the potting material 43. The electrical connections that transmit power to the ultrasound assembly (such as the common wires 108 and lead wire 110 of FIGS. 5 and 6) are not shown in FIG. 15A for simplicity. FIG. 15B illustrates an alternative heat sink configuration for use with a fluid dissipating medium. As shown in FIG. 15B, the ultrasound assembly 42 is coupled to an inner luminal surface of the cylindrical body 35 of the inner core 34. The inner core 34 defines a lumen 360 to receive cooling fluid as a dissipating medium. The ultrasound assembly is coupled to the heat sink 351 (shown as braided thermally conductive elements, but could alternatively be cooling fins). A cooling fluid is introduced into and driven through the lumen 360 of the inner core 34 (as indicated by arrow 362). The heat sink 351 then dissipates heat from the ultrasound assembly 42 into the cooling fluid.

A thermoelectric cooling element provides localized cooling of sensors and devices through use of the Peltier effect to create a heat flux. Thermoelectric cooling elements include a first and a second substrate separated by two or more semi-conductors wires 355 (such as alternating p-types and c-types), as shown in FIG. 15A. When the semi-conductors wires are connected to each other by a positive and negative power source, heat is transferred from the first substrate, which effectuates cooling of the first substrate, to the second substrate, which effectuates heating of the second substrate. The semi-conductor wires 355 may be coupled to the positive and negative power source at the proximal end 14 of the catheter system 10. The heated substrate is typically associated with a heat sink that acts to dissipate the heat away from the second substrate. As used herein, the substrates of the thermoelectric cooling element can be coupled to or formed as part of the backing of the ultrasound radiating members 42. Preferably, the cooling substrate is directly coupled to the ultrasound radiating member backing, and the heated substrate is coupled to a heat sink as described above. The combination of the thermoelectric cooling element with a heat sink ideally cools the ultrasound assembly while safely dissipating heat along the length of the inner core 34. FIG. 16 depicts a simplified diagram of the cooling element formed from both the thermoelectric cooling element in combination with a heat sink. As shown, the thermoelectric cooler is sandwiched between and ultrasound radiating member and the heat sink.

In still other embodiments, the catheter 10 further comprises an occlusion device (not shown) positioned at the distal exit port 29. The occlusion device preferably has a reduced inner diameter that can accommodate a guidewire, but that is less than the inner diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 9A, the tubular body 12 further comprises one or more temperature sensors 20, which are preferably located within the energy delivery section 18. In such embodiments, the proximal region 14 of the tubular body 12 includes a temperature sensor lead wire (not shown) which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 10:
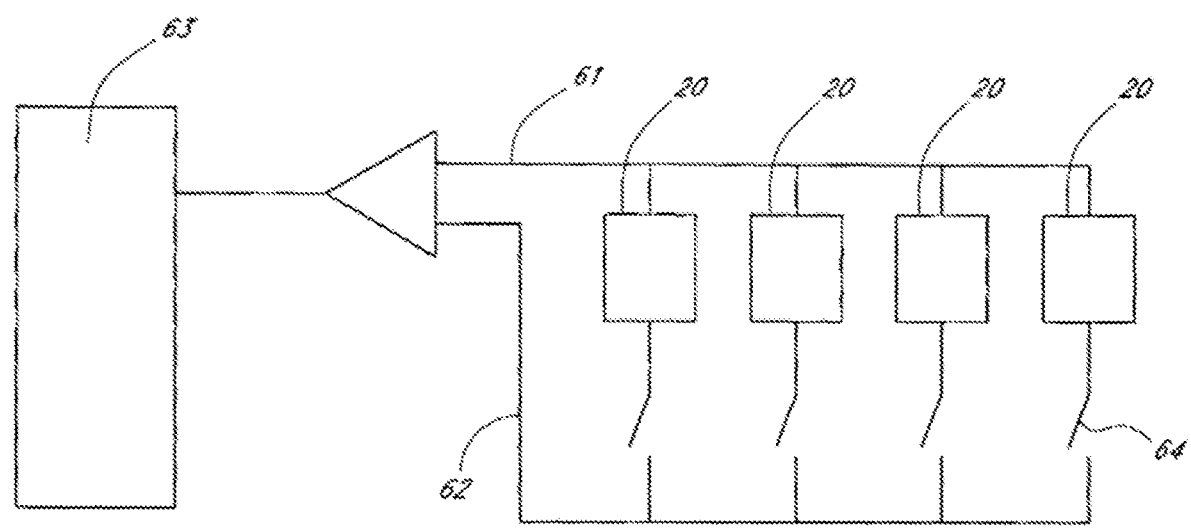
FIG. 10 illustrates an embodiment for electrically coupling temperature sensors of the catheter system.

FIG. 10 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires pass through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 9B:
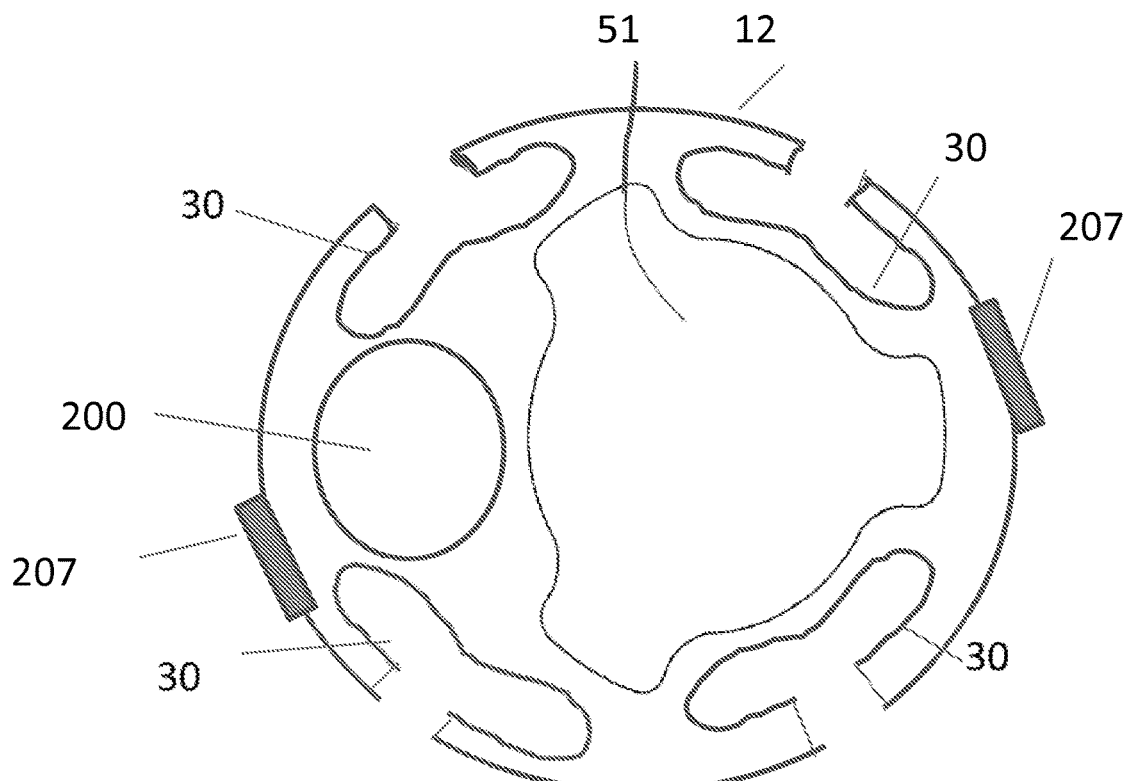

Alternatively or in addition to the one or more temperature sensors 20, the tubular body 12 includes one or more functional flow elements 207 (See FIGS. 1 and 9B). The functional flow elements 207 may include pressure sensors and/or flow sensors, which may be used to obtain functional flow data within a body lumen. Pressure sensors are able to obtain pressure measurements and flow sensors are able to obtain velocity measurements within a blood vessel. The ability to measure and compare both the pressure and flow significantly improves one's ability to monitor the success of the blockage dissolution procedure. In addition, the functional flow elements 207 may be advantageously used to determine the location of a blockage, and thus the ideal location for ultrasonic therapy for blockage dissolution. Techniques for obtaining functional flow data (such as coronary flow reserve, fractional flow reserve, and pressure-volume (P-V) curves/loops) from function flow elements 207 is described in more detail hereinafter.

In further aspects, catheter systems 10 of the invention include one or more dissolution elements. The one or more dissolutions elements may include one or more balloon elements, one or more heating elements, one or more steam elements, and combinations thereof. These dissolution elements are described hereinafter. According to certain embodiments, the dissolution elements are separate from thrombolytic, drug, or other reagent-based mechanisms for dissolution, but may be used in addition to thrombolytic, drug, or other reagent-based mechanisms for dissolution.

In some embodiments, catheter systems 10 of the invention include one or more steam lumens. The steam lumens are used to disperse steam into the blockage. The heat from the steam helps soften the clot, and may even assist in breaking down the clot mechanically. The steam may be dispersed before, during, or after application of energy (such as ultrasonic) from the inner core 34 of the catheter system 10. In certain embodiments, the steam includes a thrombolytic agent, and disperses the thrombolytic agent into the clot.

The one or more steam lumens may be the same as or different from the fluid delivery lumens 30 of the tubular body 12. When the steam lumens are the same as the fluid delivery lumens 30, the therapeutic compound inlet port 32 (FIG. 1) connected to the fluid delivery lumens 30 at the proximal region 14 may be associated with a fluid/steam source that is able to convert liquid into steam for delivery into the lumens 30. The steam is emitted from the fluid delivery lumens 30 through the fluid delivery ports 58 within the tubular body energy delivery section 18 of the tubular body 12 (See, e.g., FIG. 12B). In certain embodiments, the fluid/steam source alternates between delivering steam and fluid through the fluid delivery lumens 30 as desired during the procedure.

Figure 9C:
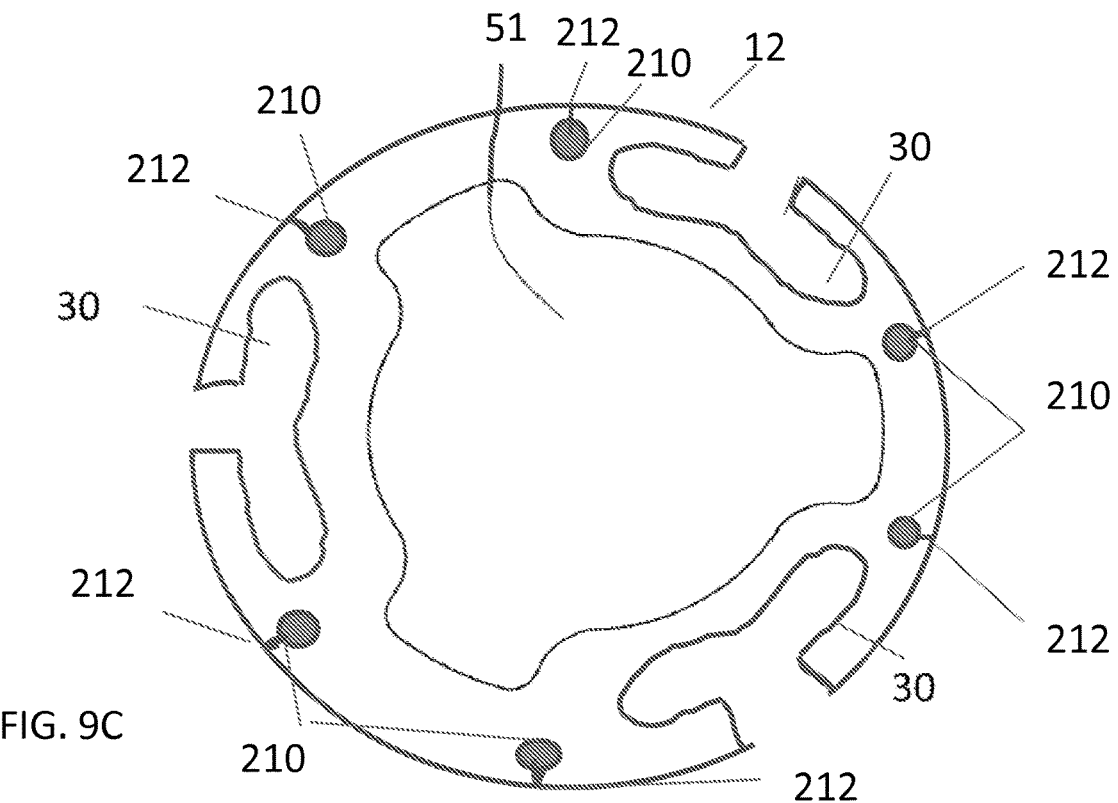

Alternatively, the steam lumens are different from the fluid delivery lumens 30. As shown in FIG. 9C, the tubular body 12 includes one or more lumens 210 to deliver steam out of the tubular body 12 and into an occlusion within the vessel. The steam lumens 210 may be used as an alternative to the fluid delivery lumens 30 (e.g. replace the fluid delivery lumens), or the steam lumens 210 may be used in conjunction with the fluid delivery lumens 30. The steam lumens 210 are associated with one or more exit ports 212 at the distal portion 15 of the tubular body 12, and are coupled to a steam source at the proximal end 14 (similar to the fluid source coupled to the fluid delivery lumens described above). Although not shown, the steam lumens 210 are coupled to a proximal port (similar to the therapeutic compound inlet port 32 shown in FIG. 1) that couples to a steam source.

In certain embodiments, the steam includes thrombolytic agents and other medicine. In these embodiments, the thrombolytic steam assists in breaking down the thrombus and/or plaque. The thrombolytic steam may be introduced in to the occlusion before, during, or after application of the ultrasonic energy. In other embodiments, the steam delivered from steam lumens 210 is used in conjunction with thrombolytic agents introduced separately out of fluid delivery lumens 30. For example, thrombolytic agents are introduced into the occlusion from the fluid delivery lumens 30, after which steam is introduced into the vessel to further drive the thrombolytic agents into the clot.

Figure 13A:
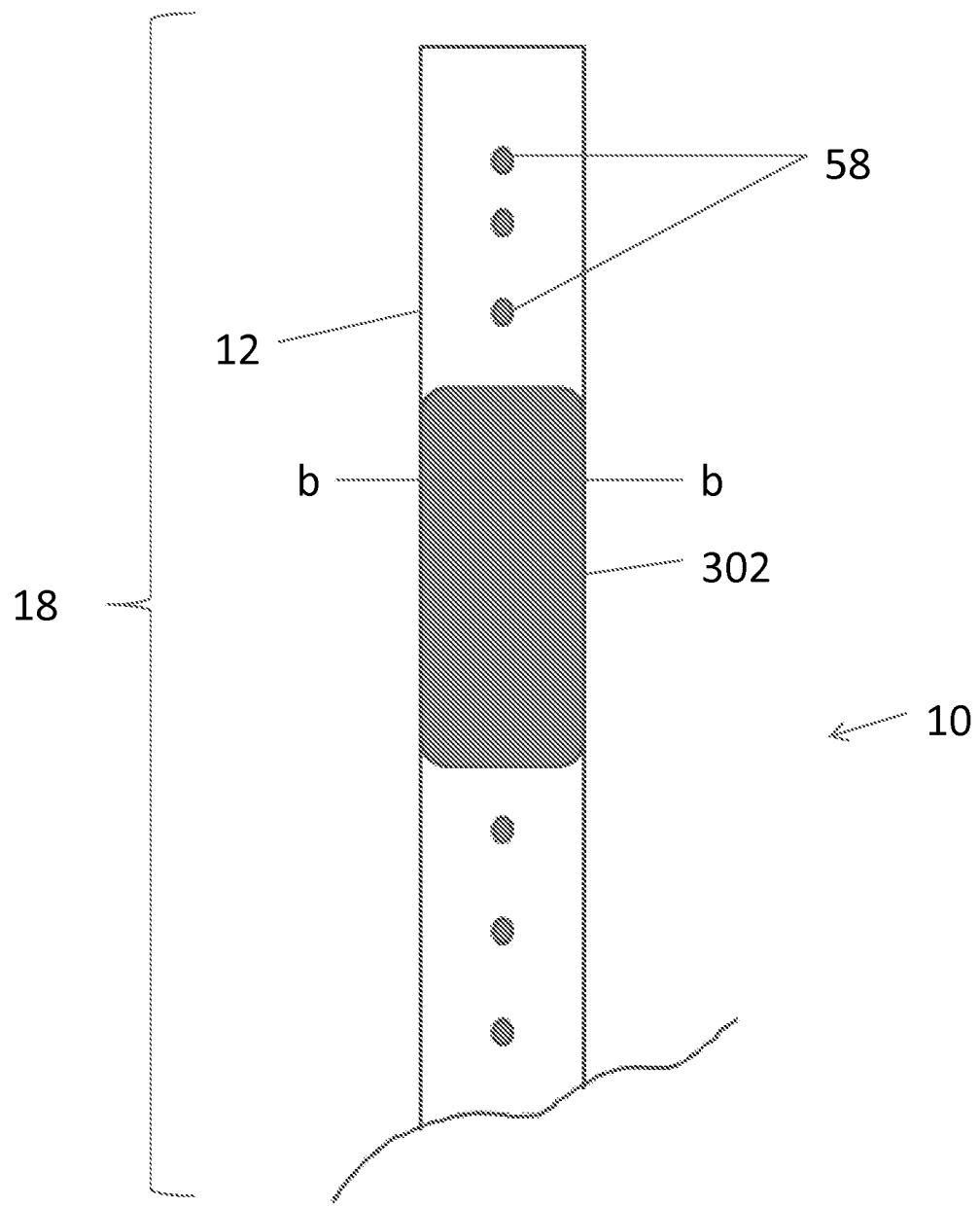
FIGS. 13A-13C illustrate embodiments of the catheter system with a balloon element.
Figure 13B:
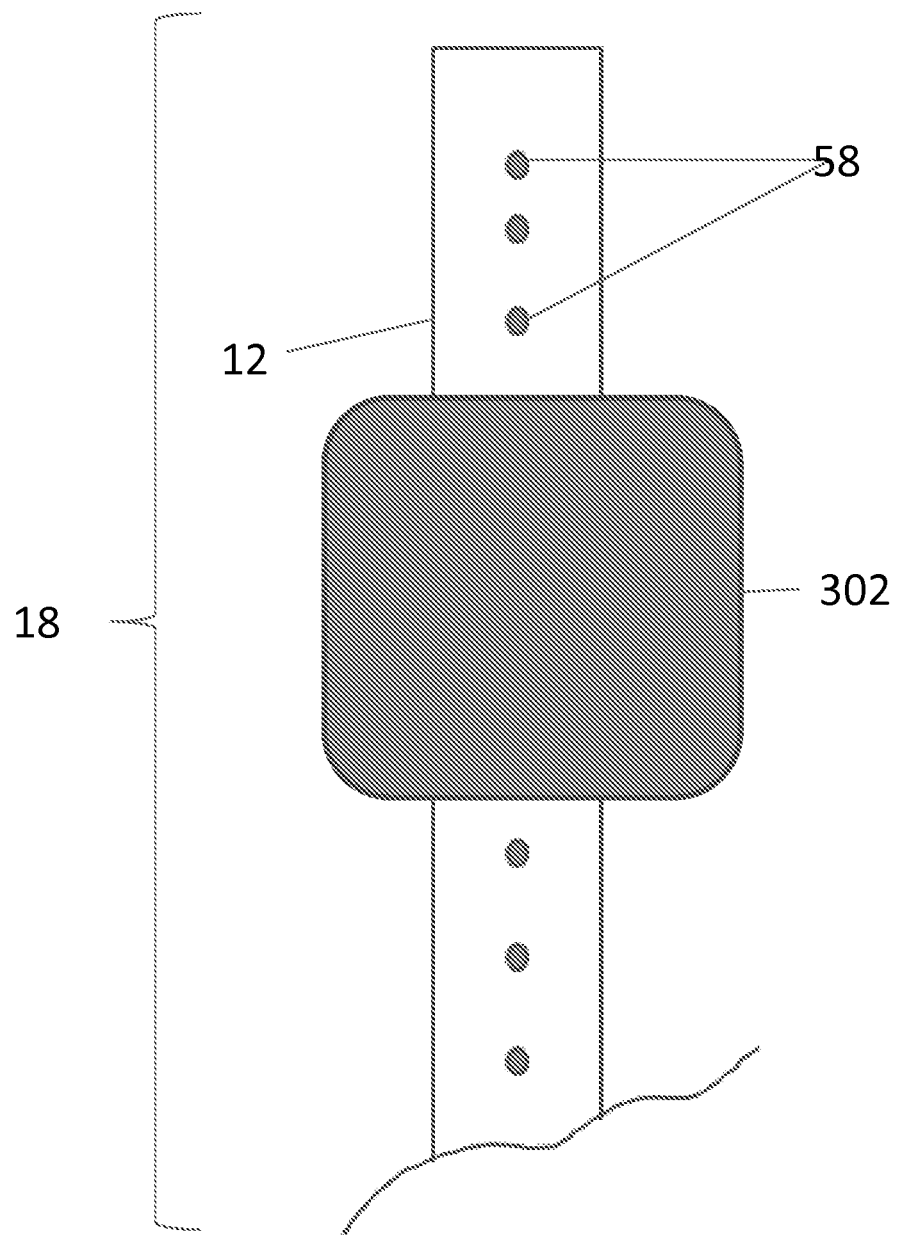
Figure 13C:
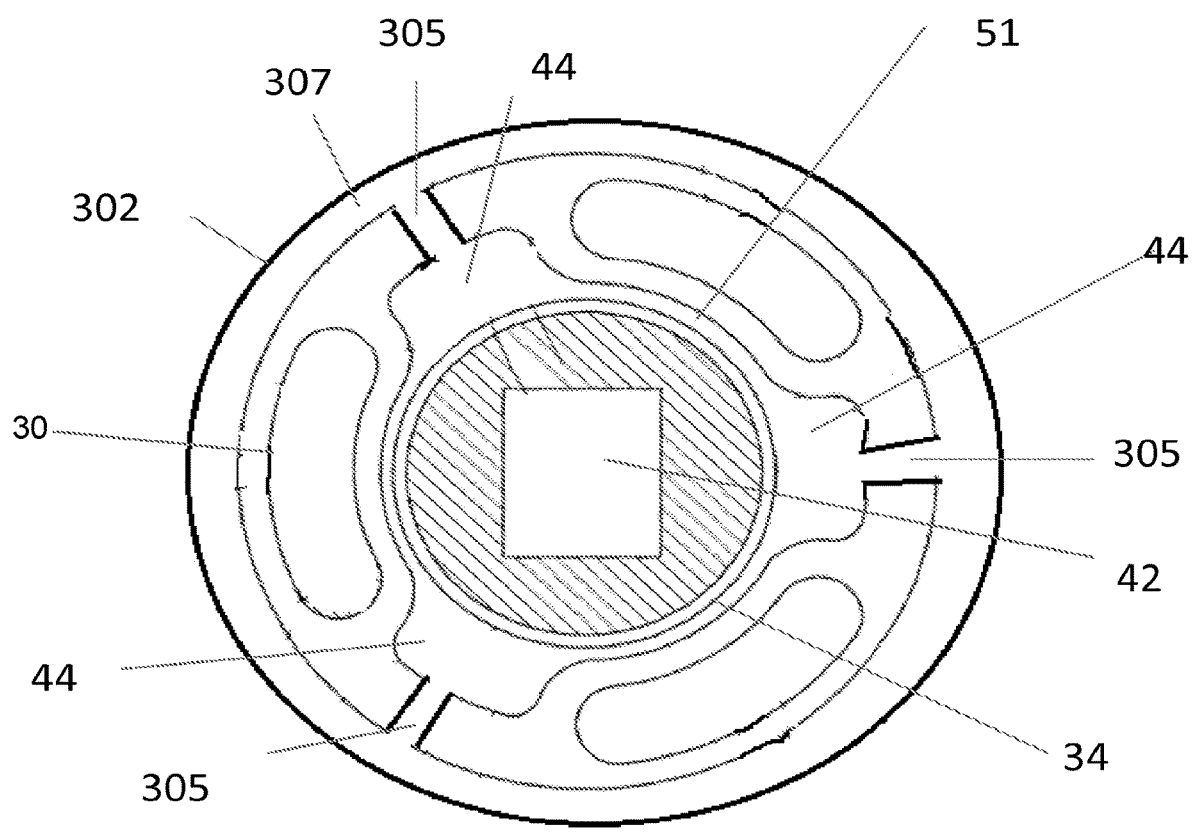

In some embodiments, catheter systems 10 of the invention further comprise a balloon element 302 operably associated with the tubular body energy delivery section 18 of the tubular body 12. The balloon element 302 may be proximal or distal to fluid delivery ports 58 (and/or steam delivery ports) located on the distal delivery section 18. FIG. 13A illustrates an embodiment of the catheter system 10 with a balloon 302. As depicted, the catheter system 10 includes a balloon 302 located between the fluid delivery ports 58 of the tubular body 12. The balloon 302 may be inflated as shown in FIG. 13B. When inflated, the balloon 302 serves to assist in breaking down and/or compressing the blockage within the vessel. Preferably, the balloon 302 is formed from a material that is transparent to acoustic energy such that it allows therapeutic energy emitted from the elongate inner core 34 to transmit through the balloon 302. The balloon 302 may be coupled to one or more balloon lumens that delivery a fluid or other substance into the balloon for inflation. In one embodiment shown in FIG. 13C, the balloon 302 is operably associated with the cooling fluid lumens 44, and the cooling fluid lumens 44 deliver fluid into the balloon 302 for expansion while serving the dual purpose of cooling the ultrasound transducer assembly 42 of elongated inner core 34. FIG. 13C illustrates a cross-section of the intraluminal device 10 along the line b of FIG. 13A. As further shown in FIG. 13C, cooling fluid leaves the cooling lumens 44 through ports 305 to fill the inside 307 of the balloon 302, thereby inflating the balloon 302.

Figures 14A, 14B:
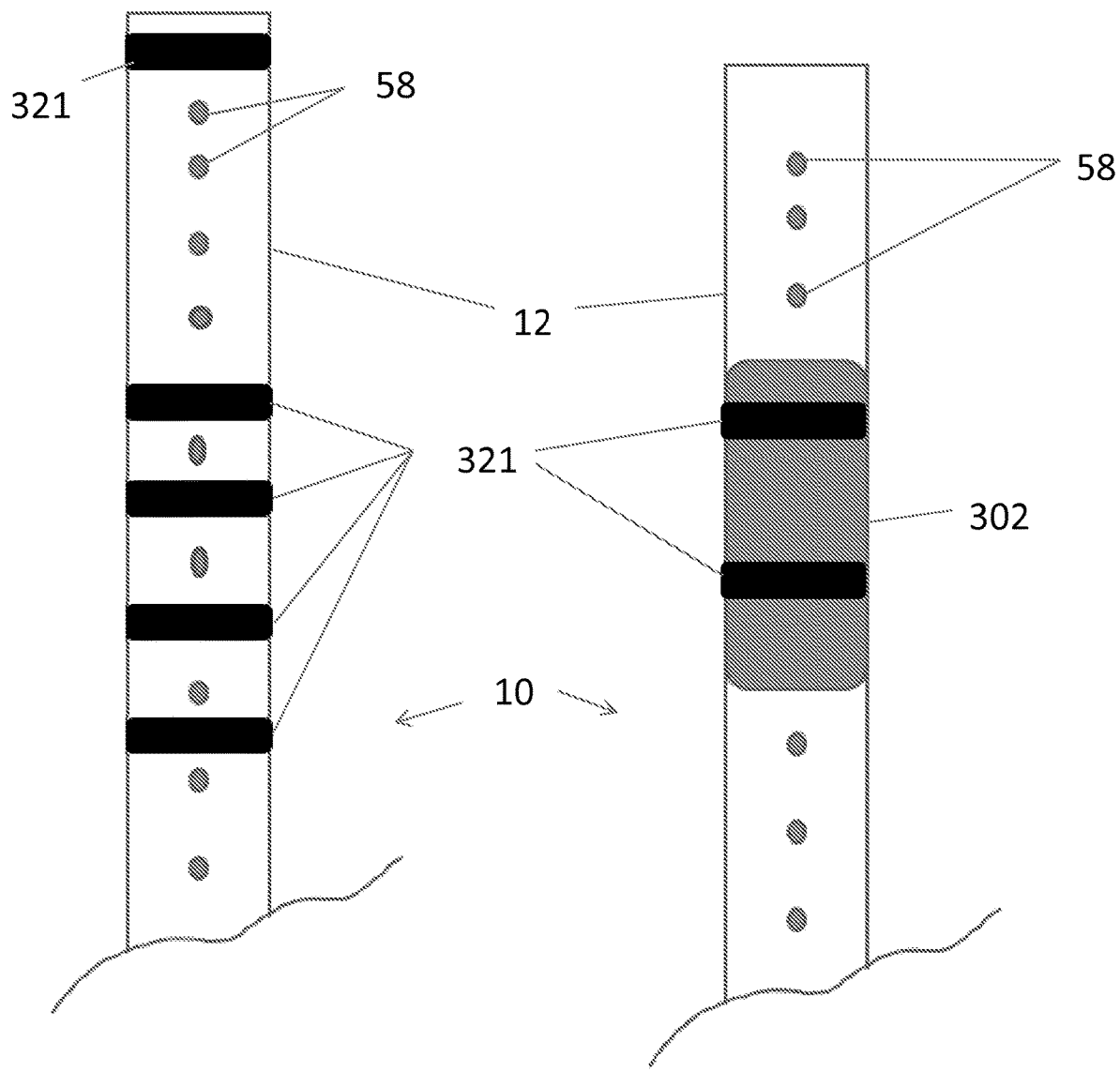
FIGS. 14A-14B illustrate embodiments of the catheter system with a heating element.

In further embodiments, the catheter system 10 may additionally include one or more heating elements 321 located on or coupled to the tubular body 12. The heating element(s) 321 apply heat, such as ablative heat, directly to the blockage. The heating element(s) 321 can be located directly on the tubular body 12 or on a balloon associated with tubular body 12 (such as balloon 302). Particularly, the heating elements 321 may be located on the side of the tubular body 12 or balloon for heating clot/atheroma material parallel to the tubular body and/or distal end for heating clot/atheroma material in front of the tubular body. The heating element 321 can apply heat simultaneously with the application of energy from the ultrasound assembly 42 of inner core 34 or intermittently between applications of the energy from the ultrasound assembly 42 of the inner core 34. FIG. 14A illustrates an embodiment of the catheter system 10 with one or more heating elements 321 disposed on the tubular body 12. As shown, the heating elements are dispersed around the fluid delivery ports 58. FIG. 14B illustrates an embodiment of the catheter system 10 with one or more heating element 321 disposed on the balloon 302 of the tubular body 12.

In particular embodiments, the one or more heating elements 321 associated with the tubular body 12 are electrodes. The electrodes may be connected to an energy source via power wires running along the length of the tubular body. The electrodes can be arranged in many different patterns along the ablation tool. For example, the electrode may be located on a distal end of the ablation tool. In addition, the electrodes may have a variety of different shape and sizes. For example, the electrode can be a conductive plate, a conductive ring, conductive loop, or a conductive coil. The heating elements 321 may partially or fully surround the circumference of the tubular body 12. In addition, the heating elements 321 may form longitudinal panels along the length of the tubular body 12.

The electrodes are connected to an energy source at a proximal end of the intraluminal device 10 that provides energy to the electrodes. In certain embodiments, the energy supplied to the electrodes is ablative energy. The ablative energy may be used to dissolve the blockage within the vessel. The energy necessary to ablate blood clot and/or atheroma can be provided from a number of different sources including radiofrequency, laser, microwave, ultrasound and forms of direct current (high energy, low energy and fulgutronization procedures). Radiofrequency (RF) has become the preferred source of energy for ablation procedures. Any source of energy is suitable for use with the heating elements 321. Preferably, the source of energy chosen does not disrupt the imaging of the vessel during the procedure or the application of energy applied from the ultrasound assembly 42 of the inner core 34. The heating elements may be used for monopolar or bipolar application of energy. For delivery of monopolar energy, a ground electrode is used, either on the catheter shaft, or on the patient's skin, such as a ground electrode pad. For delivery of bipolar energy, adjacent electrodes are axially offset to allow bipolar energy to be directed between adjacent circumferential (axially offset) electrodes. In other embodiments, electrodes may be arranged in bands around the balloon 302 to allow bipolar energy to be directed between adjacent distal and proximal electrodes. During application of the heat from the heating element, the treatment zone is typically elevated to 50° C. or greater, e.g., 55° C. or greater, e.g., 60° C. or greater, e.g., 65° C. or greater, e.g., 70° C. or greater. In some embodiments the treatment zone is heated to about 65° C., e.g., 68° C.

Once the tubular member 12 of the intraluminal device 10 is positioned within the treatment zone (e.g. as guided with the imaging elements and/or functional flow elements), the heating element 321 may be engaged to apply energy to the blood clot or atherosclerotic material. When the heating elements 321 are located on a surface of balloon 302, the balloon 302 may be inflated prior to application of energy to the heating element 321. Most treatments are in the 1 to 6 Watt range, and are performed for the duration of 0.5 to 6 seconds. The use of temperature sensors (such as temperature sensors 20 or external temperature sensors placed on the tubular body 12) provides that healthy surrounding tissue is not overheated, and that the occlusion is heated enough to affect the desired dissolution. In some embodiments, the power and duration may also be gated to assure that the delivered energy does not cause severe damage to the tissue surrounding the occlusion.

In certain embodiments, heating element 321 is a laser (such as an excimer laser). In these embodiments, the laser is configured to ablate atherosclerotic material in front of the distal tip of the tubular body 12. The laser may be used in conjunction with the heating elements shown in FIGS. 14A-14B. The laser includes one or more optical fibers disposed within the tubular body 12 of the catheter 10 and the optical fibers have active end located on a distal end of the tubular body 12. With the laser located on the distal end, the catheter 10 is able to ablate any blockages located in front of the catheter 10. For example, the tubular body of the catheter, due to its width, may not be able to enter the blockage in order to position the ultrasound assembly parallel to the treatment site for blockage dissolution. This is especially true in the case of total chronic occlusions. In such cases, it may be necessary to form a path within the occlusion such that the energy delivery section 18 of the catheter 10 can be positioned within the blockage. Using the laser located on the distal end of the tubular body 12, one is advantageously able to form a path within the blockage in front of the tubular body 12, which allows the tubular body 12 to move into the blockage in order to proceed with the therapeutic energy treatment of the blockage.

Figure 17A:
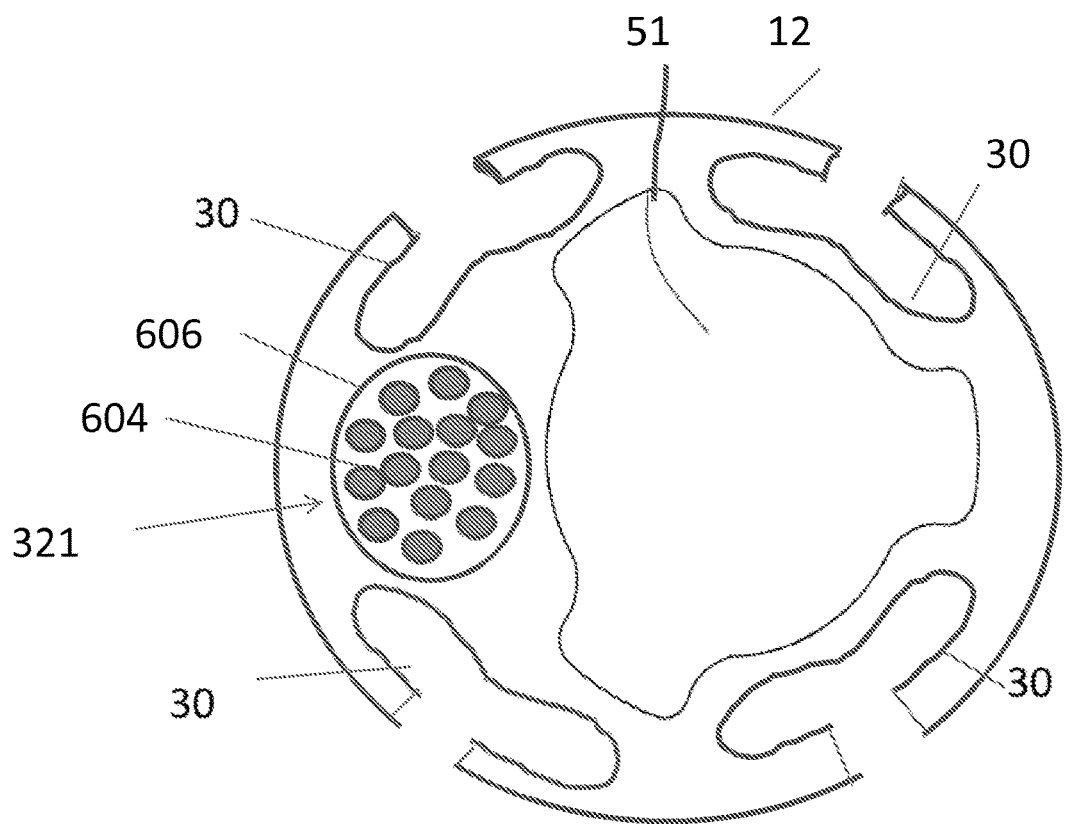
FIGS. 17A-17B illustrate embodiments of the catheter system with a laser heating element.
Figure 17B:
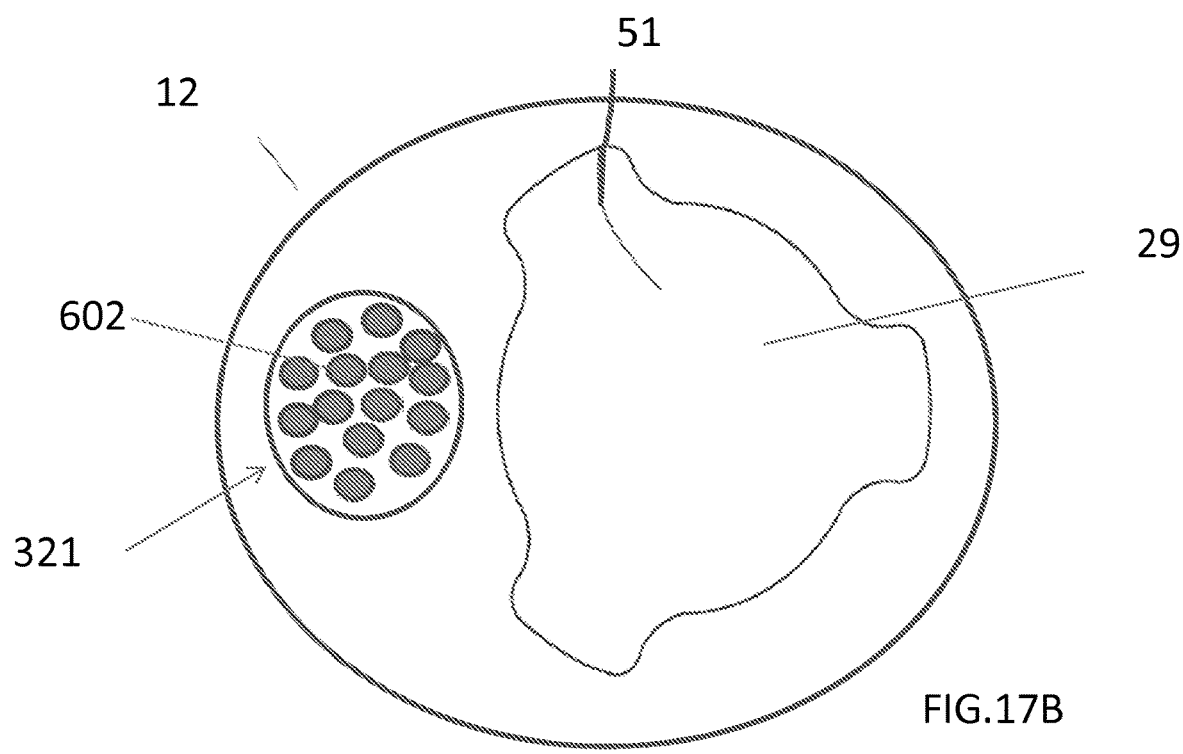

FIG. 17A depicts a cross-section (line 2-2 of FIG. 1) of the tubular body 12 with a laser heating element 321, according to certain embodiments. As shown in FIG. 17A, the tubular body 12 includes a laser lumen 604. One or more optical fibers 606 run through the laser lumen and terminate at the distal end 29 of the tubular body. Optical fibers 606 are of a type known in the art of laser catheters and are configured to transmit laser energy. The optical fibers 606 are connected to an energy source at the proximal end of the tubular body. FIG. 17B shows the active ends 602 of the optical fibers 606 located on the distal end of the tubular body 12. The active ends 602 are configured to emit laser energy to ablate blockages in front of the tubular body 12.

The level of laser energy emitted through the optical fibers may be varied depending on the type of blockage being ablated. The use of high laser energy of more than a fluence of 60 mJ/mm2 and more than 40 Hertz has the specific goal of effectively treating heavily calcified lesions while the small tip dimension allows the high laser energy to be delivered without excessive as bubble formation. Lower laser energy levels may be used such as a fluence of 60 mJ/mm2 at 40 Hertz to ablate holes through non-calcified tissue. Holes can be drilled through calcified tissue rapidly by emitting 2660 pulses of laser energy at a fluence of 100 mJ/mm2/80 Hertz so the fastest and best results for ablating calcified tissue is for at least a fluence of 80 mJ/mm2/80 Hertz excimer laser parameter settings. Laser energy is transmitted from a laser system into the optical fibers. Laser systems for transmitting laser energy or other ablative energy levels into optical fibers are described in more detail in U.S. Pat. Nos. 5,188,632, 5,423,806, 5,040,548 6,673,064, 5,203, 5,176,674, 5,041,108, 4,993,412, 5,032,123, and 4,834,093 along with U.S. Publication No. 2010/0152717.

In certain embodiments, the laser is an excimer laser. An excimer laser enables the disintegration of targeted tissue and can yield relatively pure disintegration without excessive thermal damage to otherwise healthy tissue. The excimer laser is a combination of argon fluoride or krypton chloride and a rare earth gas. This combination forms a laser beam having a very short wavelength and hence photons of very high energy. Excimer catheters for endovascular therapy are presently produced by the Spectranetics Corporation in the United States. The energy output, for ablating atherosclerotic tissue in coronary or peripheral arteries has a fluence of 60 mJ/mm2, 40 Hertz.

According to certain aspects, systems and methods of the invention provide for analyzing the functional flow data in order to determine the appropriate treatment site within a body lumen, and/or to assess the effectiveness of the blockage dissolution treatment (i.e. assess blood flow after the blockage has been removed). This analysis may be based on threshold levels of pressure and flow within the vessel that are indicative of a blockage within the vessel. For example, threshold levels may be established to set forth acceptable data ranges that are indicative of stenosis, vessel constriction or other vessel damage. In addition, threshold levels may be established to categorize a location within the vessel as normal or abnormal. In addition, a threshold level may be established for an intermediate range between normal and abnormal. In one embodiment, parameters for function flow data include levels for Coronary flow reserve, Fractional flow reserve, pressure-volume (P-V) curves/loops, or combinations thereof. The threshold levels and parameters related to functional flow measurements may be automatically determined by software associated with the functional flow elements or manually determined by a physician operating the intraluminal device.

Coronary flow reserve is defined as the ratio of maximal coronary flow with hyperemia to normal flow. Coronary flow reserve signifies the ability of the myocardium to increase blood flow in response to maximal exercise. A ratio at or above 2 is considered normal. Abnormal CFR (a ratio below 2) indicates stenosis, thrombus, abnormal constriction of microarteries, and combinations thereof. Coronary flow reserve measures the velocity of the flow. Fractional flow reserve measure pressure differences across a portion of a vessel to determine whether a level of constriction of the vessel or presence of a thrombus or stenosis within the vessel will impede oxygen delivery to the heart muscle. Specifically, Fractional flow reserve is a ratio of a level of pressure distal to a portion of a vessel under examination to a level of pressure proximal to a portion of a vessel under examination. Often a cut-off point is 0.75 to 0.80 has been used, in which high values indicate a non-significant stenosis or constriction and lower values indicate a significant stenosis and lesion.

P-V loops provide a framework for understanding cardiac mechanics. Such loops can be generated by real time measurement of pressure and volume within the left ventricle. Several physiologically relevant hemodynamic parameters such as stroke volume, cardiac output, ejection fraction, myocardial contractility, etc. can be determined from these loops. To generate a P-V loop for the left ventricle, the LV pressure is plotted against LV volume at multiple time points during a single cardiac cycle. The presence of a stenosis or constriction can alter the curve/shape of P-V loop from a normal P-V loop.

It has been shown that distal pressure and velocity measurements, particularly regarding the pressure drop-velocity relationship such as Fractional Flow reserve (FFR), Coronary flow reserve (CFR) and combined P-V curves, reveal information about the stenosis severity. For example, in use, the functional flow device may be advanced to a location on the distal side of the stenosis. The pressure and flow velocity may then be measured at a first flow state. Then, the flow rate may be significantly increased, for example by the use of drugs such as adenosine, and the pressure and flow measured in this second, hyperemic, flow state. The pressure and flow relationships at these two flow states are then compared to assess the severity of the stenosis and provide improved guidance for any coronary interventions. The ability to take the pressure and flow measurements at the same location and same time with a combined pressure/flow guidewire, improves the accuracy of these pressure-velocity loops and therefore improves the accuracy of the diagnostic information.

Coronary flow reserve, Fractional flow reserve, and P-V loops may require measurements taken at different locations in the artery. In order to provide measurements for these parameters, systems and methods of the invention may assess pressure and flow at a first location of the functional flow sensor against a second location of the functional flow sensor within the vasculature. For example, a first location that is distal to a segment of a vessel under examination and a second location that is proximal to that segment of a vessel. The obtained measurements across the two locations are then assessed against the one or more threshold levels, which may be used to determine whether a blockage exists within the body lumen.

Exemplary pressure sensors and flow sensors are described in U.S. Pat. Nos. 6,106,476, 5,125,137, 6,551,250 and 5,873,835.

As discussed, intraluminal devices of the invention may include one or more imaging elements (such as imaging elements 202, 205, and 218). Suitable imaging elements are described herein after. Typically, the imaging element is a component of an imaging assembly. Any imaging assembly may be used with devices and methods of the invention, such as photoacoustic imaging apparatus and intravascular ultrasound (IVUS). The imaging element is used to send and receive signals to and from the imaging surface that form the imaging data. Imaging elements of any one component of the intraluminal device 10 may different from any other component. For example, the imaging element of the tubular body 12 may be different from the imaging element of the elongate inner core 34 or elongate member 219.

Any imaging assembly may be used with devices and methods of the invention, such as optical-acoustic imaging apparatus, intravascular ultrasound (IVUS) or optical coherence tomography (OCT). The imaging element may be a forward looking imaging element or a side-looking imaging element. The imaging element is used to send and receive signals to and from the imaging surface that form the imaging data. All of the imaging elements described hereinafter may be coupled to a signal line that provide power and allow data transmission to and from the imaging element. Typically, the signal line is coupled to an imaging system, such as a computer. The signal lines may be routed through lumens already existing in components of the endoluminal valve catheter system. Alternatively, the components can be specifically designed with lumens, in which the one or more signal lines are routed therethrough. The creation of multi-lumen catheter components is known in the art.

The imaging assembly may be an intravascular ultrasound (IVUS) imaging assembly. IVUS uses an ultrasound probe attached at the distal end. The ultrasound probe is typically an array of circumferentially positioned transducers. However, it is also envisioned that the imaging element may be a rotating transducer. For example, when the puncture element is coupled to a rotary drive shaft to enable rotation of the puncture element, the imaging element may be a rotating transducer. The proximal end of the catheter is attached to computerized ultrasound equipment. The IVUS imaging element (i.e. ultrasound probe) includes transducers that image the tissue with ultrasound energy (e.g., 20-50 MHz range) and image collectors that collect the returned energy (echo) to create an intravascular image. The imaging transducers and imaging collectors are coupled to signal lines that run through the length of the catheter and couple to the computerized ultrasound equipment.

IVUS imaging assemblies produce ultrasound energy and receive echoes from which real time ultrasound images of a thin section of the blood vessel are produced. The imaging transducers of the imaging element are constructed from piezoelectric components that produce sound energy at 20-50 MHz. The image collectors of the imaging element comprise separate piezoelectric elements that receive the ultrasound energy that is reflected from the vasculature. Alternative embodiments of imaging assembly may use the same piezoelectric components to produce and receive the ultrasonic energy, for example, by using pulsed ultrasound. That is, the imaging transducer and the imaging collectors are the same. Another alternative embodiment may incorporate ultrasound absorbing materials and ultrasound lenses to increase signal to noise.

IVUS data is typically gathered in segments where each segment represents an angular portion of an IVUS image. Thus, it takes a plurality of segments (or a set of IVUS data) to image an entire cross-section of a vascular object. Furthermore, multiple sets of IVUS data are typically gathered from multiple locations within a vascular object (e.g., by moving the transducer linearly through the vessel). These multiple sets of data can then be used to create a plurality of two-dimensional (2D) images or one three-dimensional (3D) image.

IVUS imaging assemblies and processing of IVUS data are described in further detail in, for example, Yock, U.S.

Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et at., U.S. Pat. No. 5,373, 845, Seward et al., Mayo Clinic Proceedings 71(7):629-635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et at., U.S. Pat. No. 5,183, 048, Eberle et al., U.S. Pat. No. 5,167,233, Eberle et at., U.S. Pat. No. 4,917,097, Eberle et at., U.S. Pat. No. 5,135,486, U.S. Pub. 2009/0284332; U.S. Pub. 2009/0195514 A1; U.S. Pub. 2007/0232933; and U.S. Pub. 2005/0249391 and other references well known in the art relating to intraluminal ultrasound devices and modalities.

In other embodiments, the imaging assembly may be an optical coherence tomography imaging assembly. OCT is a medical imaging methodology using a miniaturized near infrared light-emitting probe. As an optical signal acquisition and processing method, it captures micrometer-resolution, three-dimensional images from within optical scattering media (e.g., biological tissue). Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety.

In OCT, a light source delivers a beam of light to an imaging device to image target tissue. Light sources can include pulsating light sources or lasers, continuous wave light sources or lasers, tunable lasers, broadband light source, or multiple tunable laser. Within the light source is an optical amplifier and a tunable filter that allows a user to select a wavelength of light to be amplified. Wavelengths commonly used in medical applications include near-infrared light, for example between about 800 nm and about 1700 nm.

Aspects of the invention may obtain imaging data from an OCT system, including OCT systems that operate in either the time domain or frequency (high definition) domain. Basic differences between time-domain OCT and frequency-domain OCT is that in time-domain OCT, the scanning mechanism is a movable minor, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference minor, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images. Thus, OCT for purposes of this invention is suitable for use with the rotatable elongate member 219 (FIG. 3A-3B) or the rotatable inner core 34.

In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously.

Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in its entirety.

In yet another embodiment, the imaging assembly is an optical-acoustic imaging apparatus. Optical-acoustic imaging apparatus include at least one imaging element to send and receive imaging signals. In one embodiment, the imaging element includes at least one acoustic-to-optical transducer. In certain embodiments, the acoustic-to-optical transducer is an Fiber Bragg Grating within an optical fiber. In addition, the imaging elements may include the optical fiber with one or more Fiber Bragg Gratings (acoustic-to-optical transducer) and one or more other transducers. The at least one other transducer may be used to generate the acoustic energy for imaging. Acoustic generating transducers can be electric-to-acoustic transducers or optical-to-acoustic transducers. The imaging elements suitable for use in devices of the invention are described in more detail below.

Fiber Bragg Gratings for imaging provides a means for measuring the interference between two paths taken by an optical beam. A partially-reflecting Fiber Bragg Grating is used to split the incident beam of light into two parts, in which one part of the beam travels along a path that is kept constant (constant path) and another part travels a path for detecting a change (change path). The paths are then combined to detect any interferences in the beam. If the paths are identical, then the two paths combine to form the original beam. If the paths are different, then the two parts will add or subtract from each other and form an interference. The Fiber Bragg Grating elements are thus able to sense a change wavelength between the constant path and the change path based on received ultrasound or acoustic energy. The detected optical signal interferences can be used to generate an image using any conventional means.

Exemplary optical-acoustic imaging assemblies are disclosed in more detail in U.S. Pat. Nos. 6,659,957 and 7,527,594, 7,245,789, 7,447,388, 7,660,492, 8,059,923 and in U.S. Patent Publication Nos. 2008/0119739, 2010/0087732 and 2012/0108943.

In certain embodiments, an imaging element is disposed beneath or on a surface of a balloon.

The imaging element may be a side-looking imaging element, a forward-looking imaging element, or combination thereof. Examples of forward-looking ultrasound assemblies are described in U.S. Pat. Nos. 7,736,317, 6,780, 157, and 6,457,365, and in Yao Wang, Douglas N. Stephens, and Matthew O'Donnellie, "Optimizing the Beam Pattern of a Forward-Viewing Ring-Annular Ultrasound Array for Intravascular Imaging", Transactions on Ultrasonics, Rerroelectrics, and Frequency Control, vol. 49, no. 12, December 2002. Examples of forward-looking optical coherence tomography assemblies are described in U.S. Publication No. 2010/0220334, Fleming C. P., Wang H., Quan, K. J., and Rollins A. M., "Real-time monitoring of cardiac radiofrequency ablation lesion formation using an optical coherence tomography forward-imaging catheter," J. Biomed. Opt. 15, (3), 030516-030513 ((2010)), and Wang H, Kang W, Carrigan T, et al; In vivo intracardiac optical coherence tomography imaging through percutaneous access: toward image-guided radio-frequency ablation. J. Biomed. Opt. 0001;16(11):110505-110505-3, doi:10.1117/1.3656966. In certain aspects, an imaging assembly includes both side-viewing and forward-looking capabilities. These imaging assemblies utilize different frequencies that permit the imaging assembly to isolate between forward looking imaging signals and side viewing imaging signals. For example, the imaging assembly is designed so that a side imaging port is mainly sensitive to side-viewing frequencies and a forward viewing imaging port is mainly sensitive to forward viewing frequencies. Example of this type of imaging element is described in U.S. Pat. Nos. 7,736,317, 6,780,157, and 6,457, 365.

Figure 11:
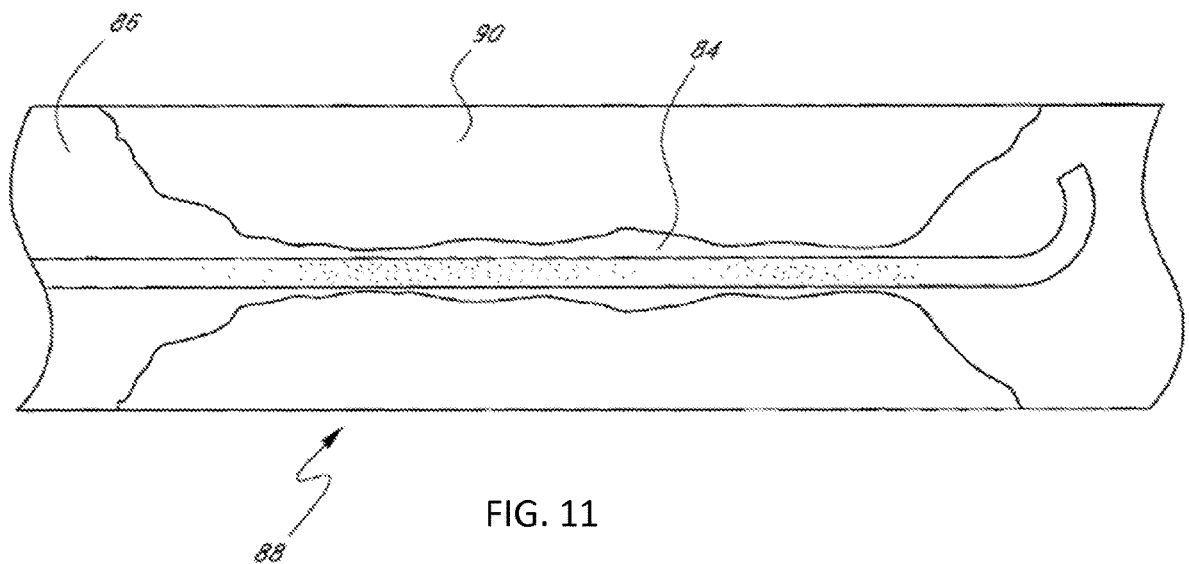
FIG. 11 depicts a guidewire inserted into a vessel for a clot dissolution procedure.
Figure 12C:
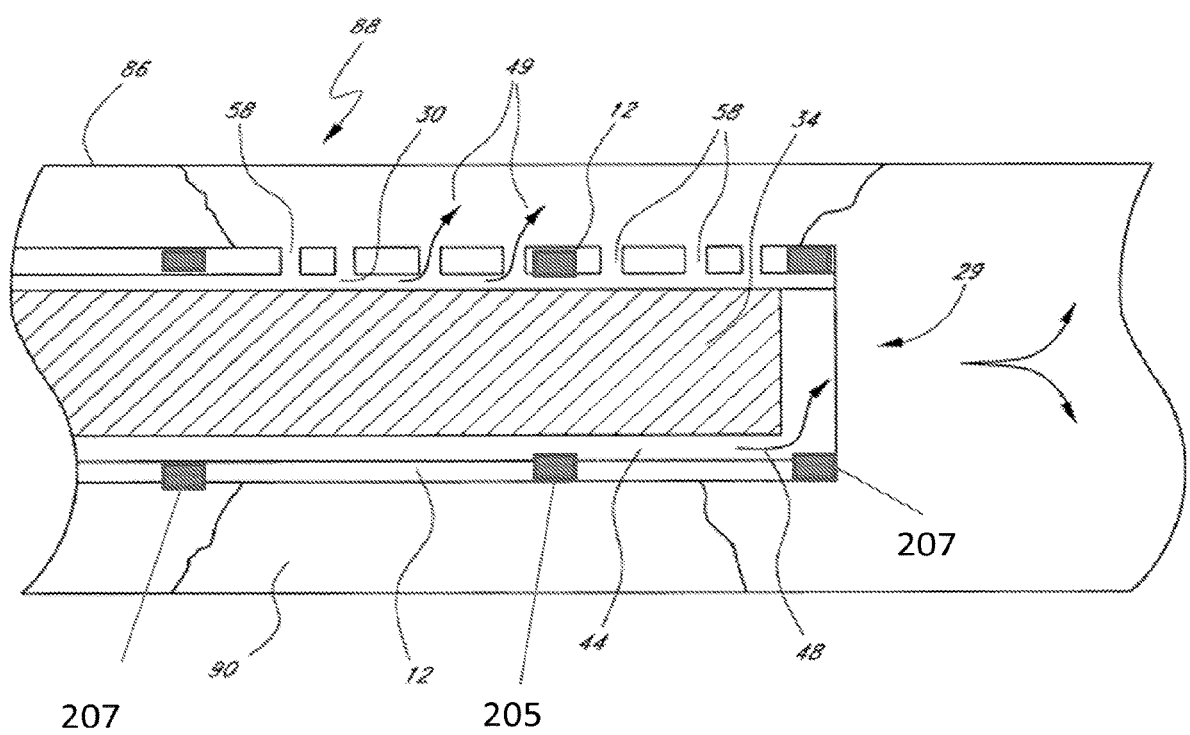

FIGS. 11 through 12C illustrate a method for using the intraluminal device 10. As illustrated in FIG. 11, a guidewire 84 similar to a guidewire used in typical angioplasty procedures is directed through a patient's vessels 86 to a treatment site 88 which includes a clot 90. The guidewire may be an imaging and/or pressure sensing guidewire, both of which are known in the art. For example, the FLOWIRE® Doppler Guide Wire, available from Volcano Corp. (San Diego, Calif.), has a tip-mounted ultrasound transducer and can be used in all blood vessels, including both coronary and peripheral vessels, to measure blood flow velocities during diagnostic angiography and/or interventional procedures. Advanced guidewires, such as FLOWIRE® can be used with the described inventions.

The guidewire 84 is directed through the clot 90. Suitable vessels 86 include, but are not limited to, the large periphery and the small cerebral blood vessels of the body. Additionally, as mentioned above, the intraluminal device 10 also has utility in various imaging applications or in applications for treating and/or diagnosing other diseases in other body parts.

As illustrated in FIG. 12A, the tubular body 12 is slid over and is advanced along the guidewire 84 using conventional over-the-guidewire techniques. The imaging element 205 of the tubular body 12 may be used to obtain real-time images of the vessel surfaces as the tubular body is advanced. The obtained imaging data may be used to determine the location of the clot 90. In addition to or as an alternative, the functional flow elements 207 may be used to determine the location of the clot 90. The tubular body 12 is advanced until the energy delivery section 18 of the tubular body 12 is positioned at the clot 90. According to aspects that include a heating element on the distal end of the tubular body 12, the heating element may be used to ablate the clot 90 in front of the intraluminal device 10 such that the tubular body 12 may be advanced until the energy delivery section 18 is positioned within the clot. In certain embodiments, radiopaque markers (not shown) are positioned along the energy delivery section 18 of the tubular body 12 to aid in the positioning of the tubular body 12 within the treatment site 88.

As illustrated in FIG. 12B, the guidewire 84 is then withdrawn from the tubular body 12 by pulling the guidewire 84 from the proximal region 14 of the catheter 10 while holding the tubular body 12 stationary. This leaves the tubular body 12 positioned at the treatment site 88.

As illustrated in FIG. 12C, the inner core 34 is then inserted into the tubular body 12 until the ultrasound assembly is positioned at least partially within the energy delivery section 18 of the tubular body 12. Once the inner core 34 is properly positioned, the ultrasound assembly 42 is activated to deliver ultrasonic energy through the energy delivery section 18 to the clot 90. As described above, in one embodiment, suitable ultrasonic energy is delivered with a frequency between about 20 kHz and about 20 MHz.

In a certain embodiment, the ultrasound assembly 42 comprises sixty ultrasound radiating members 40 spaced over a length between approximately 30 cm and 50 cm. In such embodiments, the catheter 10 can be used to treat an elongate clot 90 without requiring movement of or repositioning of the catheter 10 during the treatment. However, it will be appreciated that in modified embodiments the inner core 34 can be moved or rotated within the tubular body 12 during the treatment. Such movement can be accomplished by maneuvering the proximal hub 37 of the inner core 34 while holding the backend hub 33 stationary.

Referring again to FIG. 12C, arrows 48 indicate that a cooling fluid flows through the cooling fluid lumen 44 and out the distal exit port 29 Likewise, arrows 49 indicate that a therapeutic compound flows through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Additionally, the imaging element 205 may be used to image the progression of the ultrasonic therapy, and the functional flow elements 207 may be used to verify reestablishment of blood flow after ultrasonic therapy. Consequently, the steps illustrated in FIGS. 11 through 12C can be performed in a variety of different orders than as described above.

The therapeutic compound and ultrasonic energy are preferably applied until the clot 90 is partially or entirely dissolved, which may be confirmed with the imaging element 205 or the functional flow elements 207. Once the clot 90 has been dissolved to the desired degree, the tubular body 12 and the inner core 34 are withdrawn from the treatment site 88.

According to certain aspects, the data collected from the functional flow elements and/or imaging assembly is transmitted to an imaging engine, functional flow engine, or combined imaging/functional flow engine for processing and deliverance of the processed data to a user interface. The imaging and functional flow engine(s) may be part of an imaging system, such as an OCT or ultrasound imaging system, functional flow system, or combination thereof. A suitable combined imaging/functional flow system for use with catheter systems of the invention is the Volcano s5/s5i Imaging System with IVUS and FFR from Volcano Corporation, CA. The system may also be used to control the functional flow and imaging assembly during the procedure.

In addition, the imaging and functional flow engine(s) may be coupled to a user interface. The user interface may be incorporated into the imaging/functional flow system. For example, a user interacts with a visual interface to view images received from the imaging assembly and/or functional flow elements. Input from a user (e.g., parameters or a selection) are received by a processor in an electronic device. The selection can be rendered into a visible display.

Figure 18:
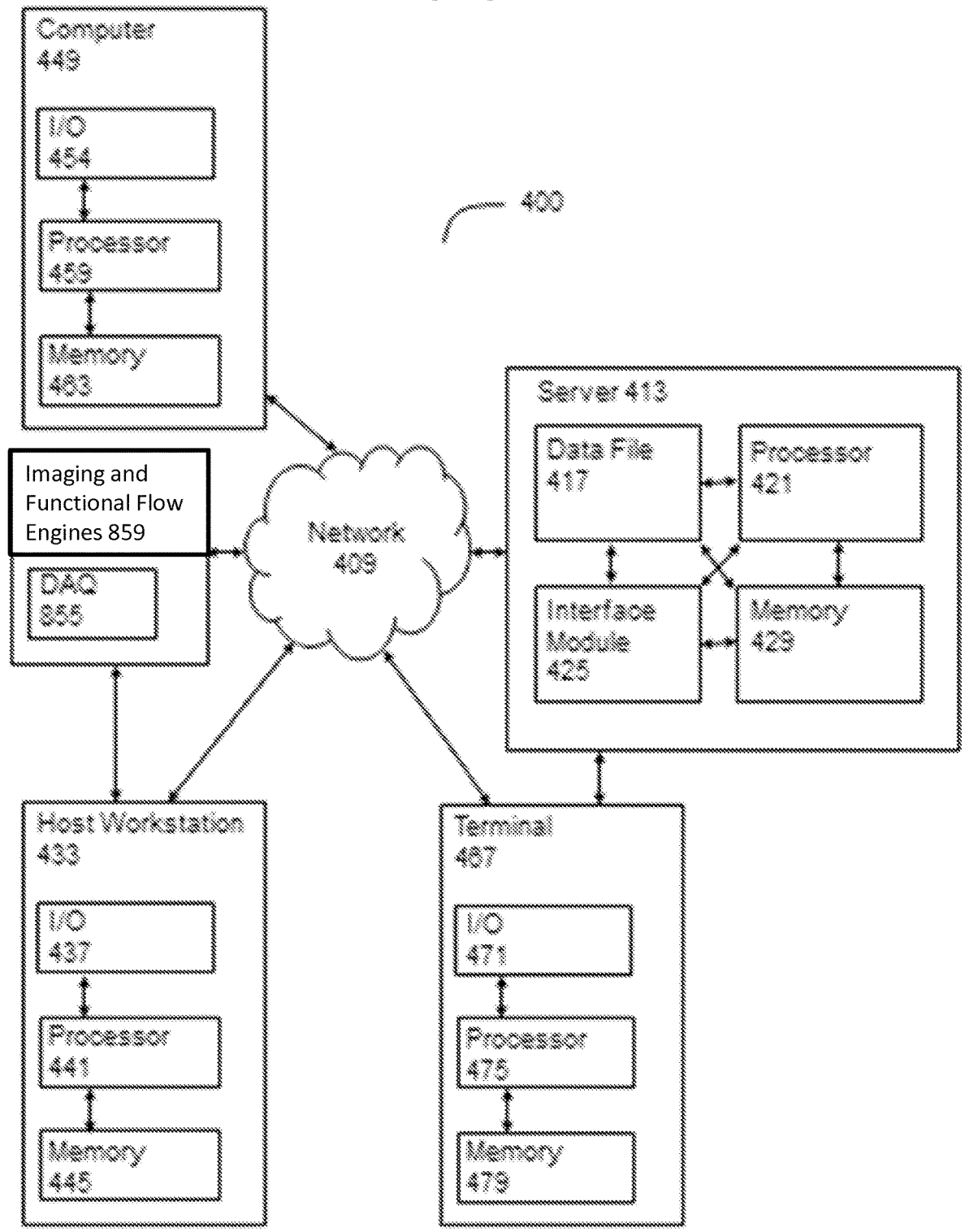
FIG. 18 illustrates a system for use with catheters of the invention.

An exemplary system configured to control the imaging elements and functional flow sensors, process data collected, and display data is illustrated in FIG. 18. As shown in FIG. 18, an imaging and functional flow engine(s) 859 communicates with host workstation 433 as well as optionally server 413 over network 409. The data acquisition element 855 (DAQ) of the imaging and functional flow engine receives data collected from the imaging element and/or functional flow elements. The engines 859 performs the necessary computations and processes on the data required for display and user interaction. In some embodiments, an operator uses computer 449 or terminal 467 to control system 400 or to receive images. An image may be displayed using an I/O 454, 437, or 471, which may include a monitor. Any I/O may include a keyboard, mouse or touchscreen to communicate with any of processor 421, 459, 441, or 475, for example, to cause data to be stored in any tangible, nontransitory memory 463, 445, 479, or 429. Server 413 generally includes an interface module 425 to effectuate communication over network 409 or write data to data file 417.

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the control of catheter system (e.g. imaging assemblies and functional flow elements) and manipulation of data collected from the imaging assemblies and functional flow elements can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

Control of the catheter system (e.g. imaging assemblies and functional flow elements) and manipulation of data collected from the imaging assemblies and functional flow elements can be implemented in a computing system that includes a back-end component (e.g., a data server 413), a middleware component (e.g., an application server), or a front-end component (e.g., a client computer 449 having a graphical user interface 454 or a web browser through which a user can interact with an implementation of the subject matter described herein), or any combination of such back-end, middleware, and front-end components. The components of the system can be interconnected through network 409 by any form or medium of digital data communication, e.g., a communication network. Examples of communication networks include cell network (e.g., 3G or 4G), a local area network (LAN), and a wide area network (WAN), e.g., the Internet.

The processing and user manipulation of the data collected from the imaging assembly and/or functional flow elements may be implemented by one or more computer programs running on the engine 859 and/or one or more processors (413, 459, 433, 475) associated with the engine 859. The one or more computer program products include one or more computer programs tangibly embodied in an information carrier (e.g., in a non-transitory computer-readable medium) for execution by, or to control the operation of the imaging and functional flow data processing system (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript. Suitable computer programs include Volcano Corporation's IVUS IMAGING: VH® IVUS Imaging System and FUNCTIONAL MANAGEMENT: ComboMap® Pressure and Flow System.

A computer program does not necessarily correspond to a file. A program can be stored in a portion of file 417 that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over network 409 (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A catheter system for delivering therapy to a body lumen, the catheter system comprising
    an elongate body defining a first lumen and comprising a distal portion;
    an inner member configured for insertion into the first lumen, the inner member comprising an acoustic energy source configured to deliver therapeutic energy to a treatment site and disrupt an occlusion within the body lumen; and
    a dissolution element coupled to the distal portion of the elongate body, wherein the dissolution element comprises a heating element configured to disrupt the occlusion, wherein the heating element is configured to be coupled to a second energy source, wherein the acoustic energy source has a structural configuration different than the heating element and the acoustic energy source is a type different than the second energy source.

2. The catheter system of claim 1, wherein the therapeutic energy is ultrasonic energy.

3. The catheter system of claim 1, wherein the inner member is configured to translate within the elongate body while delivering the therapeutic energy.

4. The catheter system of claim 1, wherein the inner member is configured to rotate within the elongate body while delivering the therapeutic energy.

5. The catheter system of claim 1, wherein the elongate body defines a delivery lumen providing a fluid path between an opening located at the distal portion of the elongated body and a port on a proximal end of the elongated body.

6. The catheter system of claim 5, wherein the delivery lumen is in fluid communication with a plurality of openings at the distal portion of the elongate body.

7. The catheter system of claim 1, wherein the heating element comprises one or more electrodes.

8. The catheter system of claim 1 further comprising a balloon.

9. The catheter system of claim 8, wherein balloon comprises the heating element.

10. The catheter system of claim 1, wherein the dissolution element is located on a distal end of the elongate body.

11. A method for delivering therapy to a blood vessel, the method comprising:
    providing a catheter system comprising:
        an elongate body defining a first lumen and comprising a distal portion;
        an inner member moveably disposed within the first lumen, the inner member comprising an acoustic energy source configured to deliver therapeutic energy; and
        a dissolution element operably associated with the elongate body, wherein the dissolution element comprises a heating element, wherein the heating element is configured to be coupled to a second energy source, wherein the acoustic energy source has a structural configuration different than the heating element and the acoustic energy source is a type different than the second energy source;
    introducing the catheter system into a blood vessel;
    operating the dissolution element at a treatment site located within the vessel;
    delivering, with the acoustic energy source, ultrasonic energy to the treatment site and
    disrupting an occlusion within the body lumen; and
    delivering, with the heating element, heat to disrupt the occlusion.

12. The method of claim 11, further comprising delivering a thrombolytic agent to the treatment site.

13. The method of claim 12, wherein the thrombolytic agent is transported through a delivery lumen of the elongate body and delivered to the treatment site through a plurality of openings located on the distal portion of the elongate body.

14. The method of claim 11, wherein the heating element comprises one or more electrodes.

15. A catheter system for delivering therapy to a body lumen, the catheter system comprising:
    an elongate body comprising a first lumen, a guidewire lumen and a distal portion;

an inner member configured for insertion into the first lumen, the inner member comprising an acoustic energy source configured to deliver therapeutic energy to a treatment site and disrupt an occlusion within the body lumen; and a dissolution element coupled to the distal portion of the elongate body, wherein the dissolution element comprises a heating element configured to disrupt the occlusion, wherein the heating element is configured to be coupled to a second energy source, wherein the acoustic energy source has a structural configuration different than the heating element and the acoustic energy source is a type different than the second energy source.

16. The catheter system of claim 15, wherein the acoustic energy source is an ultrasound transducer.

17. The catheter system of claim 16, wherein the heating element comprises one or more electrodes.

* * * * *